United States Patent
Uhl et al.

(10) Patent No.: US 6,225,080 B1
(45) Date of Patent: May 1, 2001

(54) MU-SUBTYPE OPIOID RECEPTOR

(76) Inventors: George R. Uhl, 1620 Dogwood Hill Rd., Towson, MD (US) 21204; C. Mark Eppler, 162 Bateman Rd., Langehorne, PA (US) 19047; Jai-Bel Wang, 108 Regesger Ave., Baltimore, MD (US) 21212

(*) Notice: Subject to any disclaimer, the term of this patent is extended or adjusted under 35 U.S.C. 154(b) by 0 days.

(21) Appl. No.: 08/430,286

(22) Filed: Apr. 28, 1995

Related U.S. Application Data

(63) Continuation of application No. 08/075,447, filed on Jun. 11, 1993, now abandoned, which is a continuation-in-part of application No. 08/026,140, filed on Feb. 26, 1993, now abandoned, which is a continuation-in-part of application No. 07/855,286, filed on Mar. 23, 1992, now abandoned.

(51) Int. Cl.$^7$ ............................ C12P 21/06; C12P 21/04; C07H 21/04; C12N 1/20
(52) U.S. Cl. ................. 435/69.1; 435/240.2; 435/252.3; 435/320.1; 536/23.5
(58) Field of Search .......................... 536/23.5; 435/69.1, 435/240.2, 252.3, 320.1

(56) References Cited

U.S. PATENT DOCUMENTS

| | | | |
|---|---|---|---|
| 5,242,822 | * 9/1993 | Marullo et al. | 435/69.7 |
| 5,389,543 | * 2/1995 | Bunzow et al. | 435/69.1 |

FOREIGN PATENT DOCUMENTS

WO95/19986    7/1995  (WO).

OTHER PUBLICATIONS

Sambrook et al., p. 16.3 in *Molecular Cloning*, 2ed. (1989).*
UEDA et al., "Reconstitution of rat brain μ opioid receptors . . . " *PNAS* 85: 7013–7017, (Sep. 1988).*
Evans et al., "Cloning of a Delta Opioid Receptor by Functional Expression" *Science* 258:1952–1955, (Dec. 1992).*
Chen et al., "Molecular Cloning and Functional Expression of a μ-Opioid Receptor from Rat Brain", *Mol. Pharmacol* 44(1):8–12, (Jul. 1993).*
Yinchang et al, "Solubilization and Purification of Opioid Receptor Molecules of Rat Brain" *Proc. CAMS and PUMC* 4(1):1–7 Mar. 1989.*
Gioannini et al., "Purification of an Active Opioid-binding Protein from Bovine Striatum", *J. Biol. Chem.* 260(28): 15117–15121 (Dec. 1985).*
Kieffer et al., "The S-opioid receptor: Isolation of a cDNA . . . " *PNAS* 89:12048–12052 (Dec. 1992).*
Xie et al., "Expression cloning of a cDNA encoding a seven-helix receptor . . . ", *PNAS* 89:4124–4128 (May 1992).*
Schofield et al., "Molecular characterization of a new immunoglobulin superfamily protein . . . ", *The EMBO J.* 8(2):489–495 (Feb. 1989).*

Libert et al, "Selective Amplification and Cloning of Four New Members of the G Protein–Coupled Receptor Family", *Science* 244:569–572 (May 1989).*
Wang, J.B., et al. (1983), "μ Opiate Receptor: cDNA cloning and Expression", *Proc. Natl. Acad. Sci.*, USA, vol. 90, pp. 10230–10234.
K. Yasuda (1993), "Cloning and functional comparison of k and s opioid receptors from mouse brain", 90:6736–6740.
Bruno et al. (1992), "Molecular cloning and Funcational expression of a brain specific somatostatin receptor" *P.N.A.S., USA*, 89:11151–11155.
Bunzow, James R., et al. (1994), "Molecular cloning and Tissue distribution of a putative member of the rat opioid receptor gene family that is not a μ,δ or κ opioid receptor type", *FEBS Letters*, 347:284–288.
Fukuda K., et al. (1994), "cDNA cloning and regional distribution of a novel member of the opioid receptor family", *Febs Letters*, 343:42–46.
Chen et al., "Molecular Cloning, Tissue Distribution and Chromosomal Localization of a Novel member of the Opioid Receptor Gene Family", *FEBS Letters*, 347:279–283; 280–281. (1994).
Wick et al., (1993), "Isolation of a Novel cDNA Encoding a Putative Member Receptor with High Homology to the Cloned μ, δ and κ Opioid Receptors" *Molecular Brain Research*, 27:37–44; 39–43.
Coscia et al. (1991), "A Monoclonal Anti–idiotypic Antibody to μ, and δ Opioid Receptors", *Molecular Brain Research* 9:299–306; 300–303.
Jaffe et al., *The Pharmacological Basis of Therapeutics*, 22:491–531, 1985.
Goldstein et al., *Opiods: Past, Present and Future*, 10:127–143, 1984.
Lord et al., *Nature*, 267:495–499, 1977.
Schulz et al., *J. Pharmacol. Exp. Ther.*, 216:604–606, 1981.
Loh et al., *Ann. Rev. Pharmacol. Toxicol.*, 30:123–147, 1990.
Birnbaumer et al., *Biochem. Biophys. Acta.*, 1031:163–224, 1990.

(List continued on next page.)

*Primary Examiner*—Gary L. Kunz
*Assistant Examiner*—Robert S. Landsman
(74) *Attorney, Agent, or Firm*—Darby & Darby

(57) ABSTRACT

Isolated DNA encoding mu-subtype opioid receptor polypeptides is provided. Recombinant cloning vectors which include this DNA and cells that incorporate these vectors are also provided. Methods for producing these receptors and purifying them from native and heterologous sources are also disclosed.

6 Claims, 27 Drawing Sheets

OTHER PUBLICATIONS

Bidlack et al., *PNAS USA*, 78:636–639, 1981.
Maneckjee et al., *PNAS USA*, 82:594–598, 1985.
Cho et al., *PNAS USA*, 83:4318–4149, 1986.
Ueda et al., *Neurosci. Lett*, 75:339–344, 1987.
Simon et al., *Neuropeptides*, 75:339–344, 1987.
Ahmed et al., *Life Sciences*, 44:861–871, 1989.
Laemmli et al., *Nature*, 227:680–685, 1970.
Whitehead et al., *Nature*, 305:158–159, 1983.
Merril et al., *Science*, 211:1437–1438, 1981.
Wessel et al., *Anal. Bioch.*, 138:141–143, 1984.
Blume et al., *PNAS USA*, 75:1713–1717, 1978.
Childers et al., *Life Sciences*, 23:759–762, 1978.
Bidlack et al., *J. Biol. Chem.*, 261:15844–15849, 1989.
Bidlack et al., *J. Biol. Chem.*, 260:15655–15661, 1991.
Roy et al., *BBRC*, 150:237–244, 1988.
Roy et al., *BBRC*, 154:688–693, 1988.
Chow et al., *Mol. Pharmacol.*, 24:203–212, 1983.

* cited by examiner

```
                1                                                         50
                                                                           #
     Muor1     ..........  ..........  ..........  ..........M  RSEPTGLGCN
      DOR1     ..........  ......MEL   VPSARAELQS  SPLVNLSDAF   PSAFPSAGAN
     SOMAT     ..........  .....MFPNA  PPPLPHSSPS  SSPGGCGEGV   CSRGPGSGAA
     F-PEP     ..........  ..........  ..........  ..........   METNSSLPTN
     OBP-R     ..........  ......MASP  AGNLS.AWPG  WGWPP..PAA   LRNLTSSPAP
     NEU-K     MASVPRGENW  TDGTVEVGTH  TGNLSSALGV  TEWLALQAGN   FSSALGLPAT
     RHODOP    ..........  .....MNGTE  GPNFYVPFSN  ..........   ........AT
     B2-ADR    ..........  ..........  ..........  ..........   ......MEPH 51                                                       100
     Muor1     DSLCPQTGS.  ......P...  ....SMVTGI  TIM ALYSIVC  VVGLFGNFLV
      DOR1     ASGSPGARS.  ......AS..  ....SLALAI  AITALYSAVC   AVGLLGNVLV
     SOMAT     DGMEEPGRN.  .....SSQNG  TLSEGQGSAI  LISFIYSVVC   LVGLCGNSMV
     F-PEP     ISGGTPAVS.  ......AGY.  .....LFLDI  ITYLVFAVTF   VLGVLGNGLV
     OBP-R     TASPSPAPSW  TPSPRPGPAH  PFLQPPWAVA  LWSLAYGAVV   AVAVLGNLVV
     NEU-K     TQAPSQV...  ....RANLTN  QFVQPSWRIA  LWSLAYGLVV   AVAVFGNLIV
     RHODOP    GVVRSPF...  ......EYPQ  YYLAEPWQFS  MLAAYMFLLI   VLGFPINFLT
     B2-ADR    GNDSDFLLAP  NGSRAPGHDI  TQERDEAWVV  GMAILMSVIV   LAIVFGNVLV 101                                                      150
     Muor1     MYVIVRYTKM  KTATN IYIFN  LALADALATS  TLP.F QSVNY  LMGTWPFGTI
      DOR1     MFGIVRYTKL  KTATNIYIFN  LALADALATS  TLP.FQSAKY   LMETWPFGEL
     SOMAT     IYVILRYAKM  KTATNIYILN  LAIADELLML  SVP.FLVTST   LLRHWPFGAL
     F-PEP     IWVAG.FRMT  HTVTTISYLN  LAVADFCFTS  TLPFFMVRKA   MGGHWPFGWF
     OBP-R     IWIVLAHKRM  RTVTNSFLVN  LAFADAAMAA  LNALVNFIYA   LHGEWYFGAN
     NEU-K     IWIILAHKRM  RTVTNYFLVN  LAFSDASVAA  FNTLINFIYG   LHSEWYFGAN
     RHODOP    LYVTVQHKKL  RTPLNYILLN  LAVADLFMVF  GGFTTTLYTS   LHGYFVFGPT
     B2-ADR    ITAIAKFERL  QTVTNYFITS  LACADLVMGL  AVVPFGASHI   LMKMWNFGNF 151                                                      200
     Muor1     LCK IVISIDY  YNMFTSIFTL  CTMSV DRYIA  VCHPVKALDF  RTPRNAK IVN
      DOR1     LCKAVLSIDY  YNMFTSIFTL  TMMSVDRYIA  VCHPVKALDF   RTPAKAKLIN
     SOMAT     LCRLVLSVDA  VNMFTSIYCL  TVLSVDRYVA  VEHPIKAARY   RRPTVAKVVN
     F-PEP     LCKFVFTIVD  INLFGSVFLI  ALIALDRCVC  VLHPVWTQNH   RTVSLAKKVI
     OBP-R     YCRFQNFFPI  TAVFASIYSM  TAIAVDRYMA  IIDPLKP.RL   .SATATRIVI
     NEU-K     YCRFQNFFPI  TAVFASIYSM  TAIAVDRYMA  IIDPLKP.RL   .SATATKIVI
     RHODOP    GCNLEGFFAT  LGGEIALWSL  VVLAIERYVV  ICKPMSNFRF   .GENHAIMGV
     B2-ADR    WCEFWTSIDV  LCVTASIETL  CVIAVDRYVA  ITSPFKYQSL   LTKNKARVVI
```

FIG.9A

```
              201                                                       250
Muor1    VCNWILS.SA IGLPVMF.... .....MATT KY.R QGSIDCTLTF SHPTWYWENL
 DOR1    ICIWVLA.SG VGVPIMV... ..MAVTQP.R DGAVVCMLQF PSPSWYWDTV
SOMAT    LGVWVLS.LL VILPIVV... ..FSRTAANS DGTVACNMLM PEPAQRWLVG
F-PEP    IGPWVMA.LL LTLPVII... ..RVTTVPGK TGTVACTFNF SPWTNDPKER
OBP-R    GSIWILA.F. .....LLAFP QCLYSKIKVM PGRTLCYVQW PEGSRQHFTY
NEU-K    GSIWILA.F. .....LLAFP QCLYSKIKVM PGRTLCYVQW PEGPKQHFTY
RHODOP   VFTWIMA.LA CAAPPLVGWS RYIPEGMQCS CGVD.YYTLK PEVNNESFVI
B2-ADR   LMVWIVSGLT SFLPIQMHWY RATHKQAIDC YAKETCCDFF TNQAY.....

251                                                       300
Muor1    LK ICV..... .....FIFAF IMPVLIITVC YG.LMIL RLK SVRMLSGSKE
 DOR1    TKICV..... .....FLFAF VVPILIITVC YG.LMLLRLR SVRLLSGSKE
SOMAT    FVLYT..... .....FLMGF LLPVGAICLC YV.LIIAKMR MVPSRPAG.S
F-PEP    IKVAVAMLTV RGIIRFIIGF SAPMSIVAVS YG.LIATKIH KQGLIKSS..
OBP-R    HMIVI..... ......VLVY CFPLLIMGIT YT.IVGITLW GGEIPGDTCD
NEU-K    HIIVI..... ......ILVY CFPLLIMGVT YT.IVGITLW GGEIPGDTCD
RHODOP   YMFVV..... ........HF TIPLIVIFFC YG.QLVFTVK EAAAQQQESA
B2-ADR   .......... .AIASSIVSF YVPLVVMVFV YSRVFQVAKR QLQKIDKSEG 301                       *                               350
Muor1    K....DRN.. .......... .........L RRITRM VLVV VAVFIVCWTP
 DOR1    K....DRS.. .......... .........L RRITRMVLVV VGAFVVCWAP
SOMAT    T....QRS.. .......... .........E RKITLMVMMV VMVFVICWMP
F-PEP    .......... .......... .......... .RPLRVLSFV AAAFFLCWSP
OBP-R    KYQEQLKA.. .......... .........K RKVVKMMIIV VVTFAICWLP
NEU-K    KYHEQLKA.. .......... .........K RKVVKMMIIV VVTFAICWLP
RHODOP   TTQ...KA.. .......... .........E KEVTRMVILM VVFFLICWFP
B2-ADR   RFHAQNLSQV EQDGRSGHGL RSSSKFCLKE HKALKTLGII MGTFTLCWLP
```

FIG. 9B

```
         351                                                    400
Muor1   IHIYVI KAL  ITI.PETTF.  ...QTVSWH FC IALGYTNSCL NPVLYAFL DE
 DOR1   IHIFVIVWTL  VDINRRDPL.  ..VVAALHLC IALGYANSSL NPVLYAFLDE
SOMAT   FYVVQLVNVF  AEQDDATV..  ......SQLS VILGYANSCA NPILYGFLSD
F-PEP   YQVVALIATV  RIRELLQGMY  KEIGIAVDVT SALAFFNSCL NPMLYVFMGQ
OBP-R   YH..IYFILT  AIYQQLNRWK  YIQQVYLA.S FWLAMSSTMY NPIIYCCLNK
NEU-K   YH..VYFILT  AIYQQLNRWK  YIQQVYLA.S FWLAMSSTMY NPIIYCCLNK
RHODOP  YAGVAFYIFT  ..HQGSN...  .FGPIFMTLP AFFAKSSSIY NPVIYIMMNK
B2-ADR  FFIVNIVHVI  RA.......N  LIPKEVYILL NWLGYVNSAF NPLIYC.RSP 401                                                    450
Muor1   NFKRCF.REF  CIPTSSTIE.  .QQNSTRVRQ NTREHPSTAN TVDRTNHQLE
 DOR1   NFKRCF.RQL  CRTPCGRQE.  .PGSLRRPRQ ATTRERVTAC TPS......D
SOMAT   NFKRSFQRIL  CL...SWMD.  .NAAEEPVDY YATALKSRAY SVE..DFQPE
F-PEP   DFRERLIHAL  PASLERALT.  .EDSTQTSDT ATNSTLPSAE VALQAK....
OBP-R   RFRAGFKRAF  RWCPFIHVSS  YDELELKATR LHPMRQSSLY TVTRMESMSV
NEU-K   RFRAGFKRAF  RWCPFIQVSS  YDELELKTTR FHPTRQSSLY TVSRMESVTV
RHODOP  QFRN......  ..........  ..........  ........C MLTTLCCGKN
B2-ADR  DFRIAFQELL  CLRRSSSKTY  GNGYSSNSNG RTDYTGEQSA YQLGQEKENE 451                                                    500
Muor1   NLEAETAPLP  ..........  .......... .......... ..........
 DOR1   GPGGGAAA..  ..........  .......... .......... ..........
SOMAT   NLESGCVFRN  GTCASRISTL  .......... .......... ..........
F-PEP   ..........  ..........  .......... .......... ..........
OBP-R   VFDSNDGDSA  RSSHQKRGTT  RDVGSNVCSR RNSKSTSTTA SFVSSSHMSV
NEU-K   LFDPNDGDPT  KSSRKKRAVP  RDPSANGCSH RGSKSASTTS SFISSPYTSV
RHODOP  ILGDDEASAT  ASKTETSQVA  PA........ .......... ..........
B2-ADR  LLCEEAPGME  GFVNCQGTVP  SLSIDSQGRN CNTNDSPL.. ..........

501
Muor1   ....
 DOR1   ....
SOMAT   ....
F-PEP   ....
OBP-R   EEGS
NEU-K   DEYS
RHODOP  ....
B2-ADR  ....
```

FIG.9C

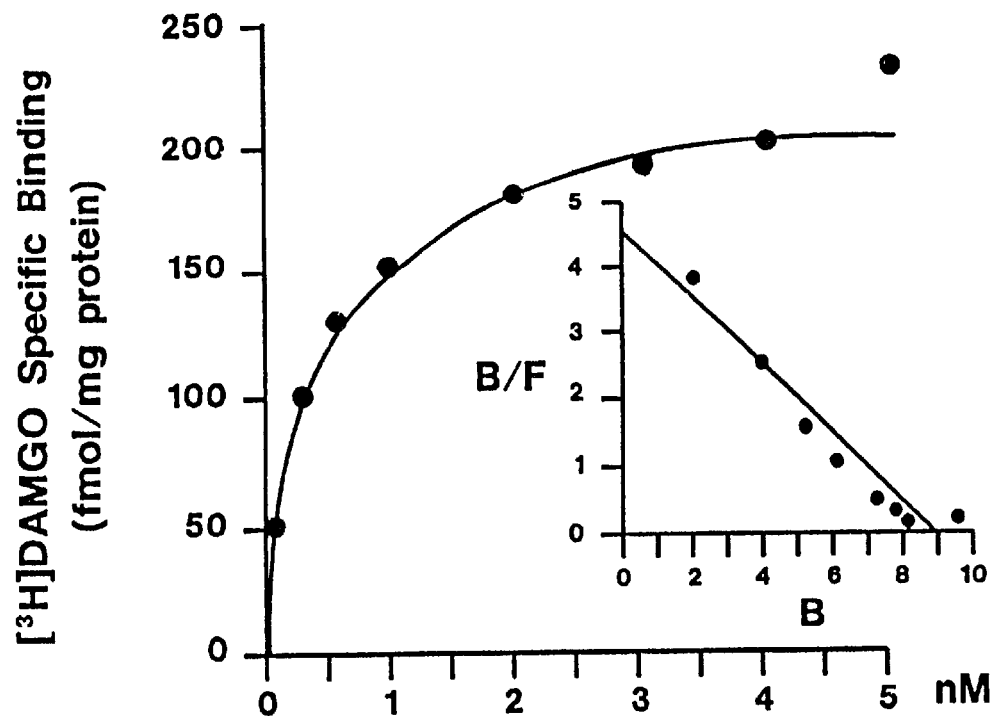
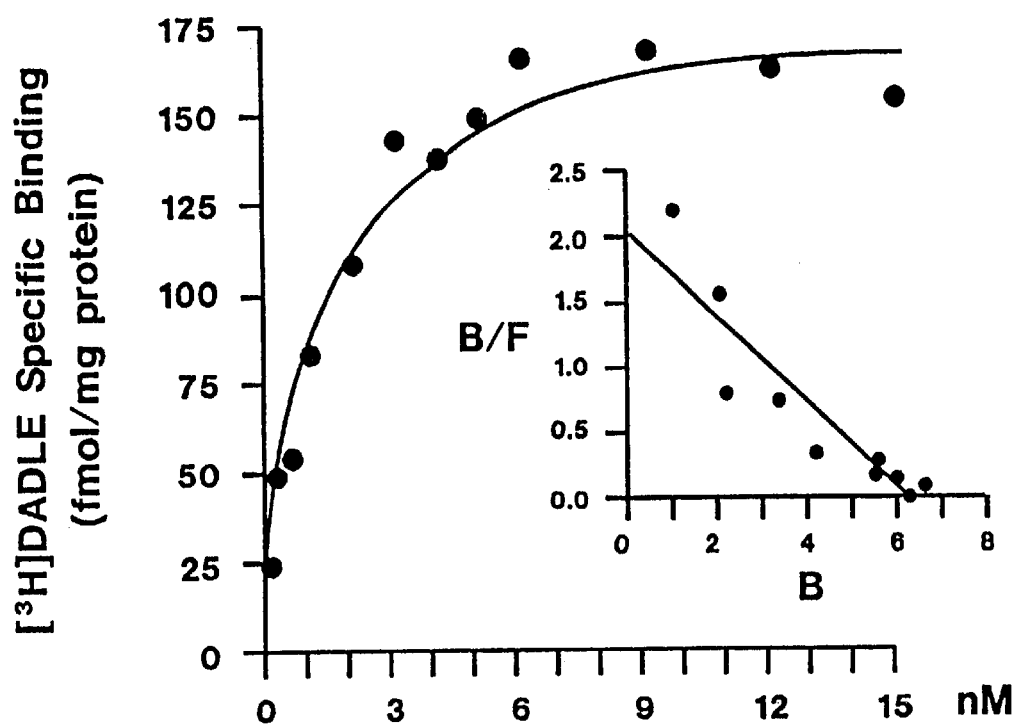
FIG. 10

```
        B   B                         E   E
   ET   p   pC                       cA PSCNc  S    C
   Acs  uD  AuvD                     olBfcvlo  c    v
   pop  Id  IIid                     RwslrioR  r    i
   oRE  Oe  uOJe                     INlmFJII  F    J
   III  II  IIII                     IIIIIIVI  I    I
    /    /  //                         ///
    GAATTCCCAGACCCCTTAGCTCAGGCAAGTTGCTCCCCAGCACCTGGCTCCTGGCTCAAC
  1 ─────────┼─────────┼─────────┼─────────┼─────────┼─────────┼ 60
    CTTAAGGGTCTGGGGAATCGAGTCCGTTCAACGAGGGGTCGTGGACCGAGGACCGAGTTG
``` b    N S Q T P * L R Q V A P Q H L A P G S T    -

```
                         S      N
      M   B              a      I              B  CS
      a   MsB    BA      uD     Aa             sMFNvc   A
      e   stc    sI      3p     cI             isocir   c
      I   IXc    rw      An     il             EpuiJF   i
      I   III    II      II     II             IIIIII   I
                          /                      ///
    TTGTCCACGTTGATGGCAACCAGTCCGATCCATGCGGTCTGAACCGACCGGGCTTGGCGG
 61 ─────────┼─────────┼─────────┼─────────┼─────────┼─────────┼ 120
    AACAGGTGCAACTACCGTTGGTCAGGCTAGGTACGCCAGACTTGGCTGGCCCGAACCGCC
``` b    C P R * W Q P V R S M R S E P T G L G G    -

```
              B
              s
              p                         MNT
         C    l       B    FnC      B   als    C
         V    2D      BsM  Mu V     sBDBeNaSp  V     BX
         i    sd      srs  n4 i     ossblcIt4  i     cc
         J    6e      lFp  IH J     JIovloly5  J     cm
         I    II      III  II I     IIIIIIII   I     II
                         //            / ////        /
    GAACGACAGCCTGTGCCCTCAGACCGGCAGCCCTTCCATGGTCACAGCCATTACCATCAT
121 ─────────┼─────────┼─────────┼─────────┼─────────┼─────────┼ 180
    CTTGCTGTCGGACACGGGAGTCTGGCCGTCGGGAAGGTACCAGTGTCGGTAATGGTAGTA
```

N HS                    S  H              E           N
    I Caa                 M  a Ca             c S         I
    a v e u      M        b  u Ve    E  M     O C         o M
    l i l 9      n        0  9 i l   a  n     R r         I s
    I J l 6      I        I  6 J I   r  I     I F         I I
    I I I I      I        I  I I I   I  I     I I         I I
       //                    /
       GGCCCTCTACTCTATCGTGTGTGTAGTGGGCCTCTTCGGAAACTTCCTGGTCATGTATGT
  181 ----------+---------+---------+---------+---------+---------+ 240
       CCGGGAGATGAGATAGCACACACATCACCCGGAGAAGCCTTTGAAGGACCAGTACATACA b   A  L  Y  S  I  V  C  V  V  G  L  F  G  N  F  L  V  M  Y  V  -

M
                            M           b               B
                            s           o               s
                            l           l               l
                            I           I               I
       GATTGTAAGATACACCAAAATGAAGACTGCCACCAACATCTACATTTTCAACCTTGCTCT
  241 ----------+---------+---------+---------+---------+---------+ 300
       CTAACATTCTATGTGGTTTTACTTCTGACGGTGGTTGTAGATGTAAAAGTTGGAACGAGA b   I  V  R  Y  T  K  M  K  T  A  T  N  I  Y  I  F  N  L  A  L  -
                                                       H
          B  p                                         i
          s  uD  H  B  R                               n           B
          a  I d g  s  s                               c           c
          H  Oe  a  r  a                               I           c
          I  I I  I  I  I                              I           I
                /
       GGCAGACGCCTTAGCGACCAGTACACTGCCCTTTCAGAGTGTCAACTACCTGATGGGAAC
  301 ----------+---------+---------+---------+---------+---------+ 360
       CCGTCTGCGGAATCGCTGGTCATGTGACGGGAAAGTCTCACAGTTGATGGACTACCCTTG
```

```
b   V  K  A  L  D  F  R  T  P  R  N  A  K  I  V  N  V  C  N  W   -
                T
             S  a
          B  M N a                              N
          s B D b l u  A l    E M  B             l
          l s p o a 3  l l    o n  c             a
          Y r n l l A  w-     r l  c             l
          l l l l V l  l l    l l  l             l
          / / / / /    /
          GATCCTCTCTTCTGCCATCGGTCTGCCTGTAATGTTCATGGCAACCACAAAATACAGGCA
      541 ———————+———————+———————+———————+———————+———————+ 600
          CTAGGAGAGAAGACGGTAGCCAGACGGACATTACAAGTACCGTTGGTGTTTTATGTCCGT b   I  L  S  S  A  I  G  L  P  V  M  F  M  A  T  T  K  Y  R  Q   -
                                                          T
             S                             E H            a
          A N a      C         M           c g S          q
          v l u      v         a    M      o i c  X  R B  l  B
          a a 9      i         e    M      R E r  c  s s  l  s
          l l 6      R         l    l      l l F  m  a l  -  r
          l V l      l         l    l      l l l  l  l l  2  l
            /                                /
          GGGGTCCATAGATTGCACCCTCACGTTCTCCCACCCAACCTGGTACTGGGAGAACCTGCT
      601 ———————+———————+———————+———————+———————+———————+ 660
          CCCCAGGTATCTAACGTGGGAGTGCAAGAGGGTGGGTTGGACCATGACCCTCTTGGACGA b   G  S  I  D  C  T  L  T  F  S  H  P  T  W  Y  W  E  N  L  L   -
                                    N S                 D M
             B         M          B l A a               r a
             s         b          s M a v u     M M     a e
             p         o          r s l a 9     n s     l l
             M         l          F p l l 6     l l     l l
             l         l          l l l l l     l l     l l
                                    / /           /
          CAAAATCTGTGTCTTTATCTTCGCTTTCATCATGCCGGTCCTCATCATCACTGTGTGTTA
      661 ———————+———————+———————+———————+———————+———————+ 720
          GTTTTAGACACAGAAATAGAAGCGAAAGTAGTACGGCCAGGAGTAGTAGTGACACACAAT
```

B
                                           s
     H B   S                       N        p
     C o c   o         B H         C  l    C N B 1
     v e e   u D P     c i     M   o  o N S   v l o 2
     i l 8   3 p l     e n     l   c  l s p   i o n 8
     J l 3   A n e     f f     y   8  l p h   J l l 6
     l l l   l l l     l l         l  l l l   l V l l
       /                                /        /
     CGGCCTGATGATCTTACGACTCAAGAGCCGTTCGCATGCTATCGGGCTCCAAAGAAAAGGA
721  ─────┼─────┼─────┼─────┼─────┼─────┼  780
     GCCGGACTACTAGAATGCTGAGTTCTCGCAAGCGTACGATAGCCCGAGGTTTCTTTTCCT b    G L M I L R L K S V R M L S G S K E L D  -

S
     H               o             S                C
     i T      H F H  u D     M A M N c B     F      v       F
     n f      p s h  3 p     s l s c r c     o      i       o
     f i      h p o  A n     p w l i F c     k      J       k
     l l      l l l  l l     l l l l l l     l      l       l
       /                /  / /
     CAGGAATCTGCGCAGGATCACCCCGGATGGTGCTGGTGGTCGTGGCTGTATTTATCGTCTG
781  ─────┼─────┼─────┼─────┼─────┼─────┼  840
     GTCCTTAGACGCGTCCTAGTGGGCCTACCACGACCACCAGCACCGACATAAATAGCAGAC b    R N L R R I T R M V L V V V A V F I V C  -

E
                                       c
              S                        o    S
     A B N o              M            4 H o    H
     v s l u     B        o            7 H o B u D   i T
     o p o 9     c        e            l h e c 3 p   n f
     l G l 6     c        l            l o l l A n   f i
     l l V l     l        l            l l l l l l   l l
       / /                               /            /
     CTGGACCCCCATCCACATCTACGTCATCATCAAAGCGCTGATCACGATTCCAGAAACCAC
841  ─────┼─────┼─────┼─────┼─────┼─────┼  900
     GACCTGGGGGTAGGTGTAGATGCAGTAGTAGTTTCGCGACTAGTGCTAAGGTCTTTGGTG

FIG.11E

''                 '
     CCCAACCTCGTCCACGATCGAACAGCAAAACTCCACTCGAGTCCGTCAGAACACTAGGGA
1021 ─────┼─────┼─────┼─────┼─────┼─────┼  1080
     GGGTTGGAGCAGGTGCTAGCTTGTCGTTTTGAGGTGAGCTCAGGCAGTCTTGTGATCCCT

E                    M              FN
                          c S        C         a              CnsP  H
                          oBc        v         Be             Avupv iT
                          Rsr        i         bl             li4Bu nf
                          IIF        R         vI             uJHII fi
                          III        I         II             IIIII II
                                                /             ////  /
         ATTTCAGACCGTTTCCTGGCACTTCTGCATTGCTTTGGGTTACACGAACAGCTGCCTGAA
    901 ────┼────────┼────────┼────────┼────────┼────────┼──── 960
         TAAAGTCTGGCAAAGGACCGTGAAGACGTAACGAAACCCAATGTGCTTGTCGACGGACTT b    F  Q  T  V  S  W  H  F  C  I  A  L  G  Y  T  N  S  C  L  N   -

E        E
                    c S      cS                                  C
              B     o c      of      F        F                  v
              s     R r      5a      o        o                  i
              r     I F      7N      k        k                  R
              I     I I      II      I        I                  I
         TCCAGTTCTTTACGCCTTCCTGGATGAAAACTTCAAGCGATGCTTCAGAGAGTTCTGCAT
    961 ────┼────────┼────────┼────────┼────────┼────────┼──── 1020
         AGGTCAAGAAATGCGGAAGGACCTACTTTTGAAGTTCGCTACGAAGTCTCTCAAGACGTA b    P  V  L  Y  A  F  L  D  E  N  F  K  R  C  F  R  E  F  C  I   -

S
              S        a  B                        H
              f        uMDsPT        M    ATXi      PF       B
              a        3npiva        I    vahn      Io       f
              N        AlnEuq        y    aqof      ak       a
              I        IIIIII        I    IIII      II       I
                         //                /
         CCCAACCTCGTCCACGATCGAACAGCAAAACTCCACTCGAGTCCGTCAGAACACTAGGGA
    1021 ────┼────────┼────────┼────────┼────────┼────────┼──── 1080
         GGGTTGGAGCAGGTGCTAGCTTGTCGTTTTGAGGTGAGCTCAGGCAGTCTTGTGATCCCT
```

FIG. 11F b   P T S S T I E Q Q N S T R V R Q N T R E  -

```
                          S
         B   C            a B                  C
         s D  v M         u cDT   A            ABv   M
         o s  i n         3 epa   l            i f i  n
         J a  J I         A fnq   w            uaJ   I
         I I  I I         I III   I            III   I
          /                //                   /
      ACATCCCTCCACGGCTAATACAGTGGATCGAACTAACCACCAGCTAGAAAATCTGGAGGC
1081  ——————+——————+——————+——————+——————+——————+ 1140
      TGTAGGGAGGTGCCGATTATGTCACCTAGCTTGATTGGTGGTCGATCTTTTAGACCTCCG
``` b   H P S T A N T V D R T N H Q L E N L E A  -

```
                                                    B
                                                    p H
                                                    u i
       A A B                        B               I n  C
       l p s     b      F B   B    B s   B          1DdMAvDM
       w a p     p      o s   s    s m   c          OdInIidn
       N B W     m      k l   r    a A   c          2eIIuJeI
       I I I     I      I I   I    I I   I          IIIIIIII
         /                         /                 / / ///
      AGAAACTGCTCCATTGCCCTAACTGGGTCTCACACCATCCAGACCCTCGCTAAGCTTAGA
1141  ——————+——————+——————+——————+——————+——————+ 1200
      TCTTTGACGAGGTAACGGGATTGACCCAGAGTGTGGTAGGTCTGGGAGCGATTCGAATCT
``` b   E T A P L P * L G L T P S R P S L S L E  -

```
         F H
       C n a     M B B   H         R          C
       v A u e B M a s s i T       I    M     v        D
       i c 4 I c s e a t n f       e    n     i        d
       J i H I c I I A X f i       A    I     J        e
       I I I I I I I I I I I       I    I     I        I
        //         / /
      GGCCGCCATCTACGTGGAATCAGGTTGCTGTCAGGGTGTGTGGGAGGCTCTGGTTTCCTG
1201  ——————+——————+——————+——————+——————+——————+ 1260
      CCGGCGGTAGATGCACCTTAGTCCAACGACAGTCCCACACACCCTCCGAGACCAAAGGAC
```

FIG.11G

```
b    A  A  I  Y  V  E  S  G  C  C  Q  G  V  W  E  A  L  V  S  *   -
                    S
                    a        C                          C          N
                    u  D     Bv                   B  v  M      CS  I
              AB    3  p     si                   s  i  n      vf  a
              lc    A  n     mR                   g  J  l      io  l
              wc    |  |     ||                   |  |  |      RN  |
              ||                /                              ||  |
              AGAAACCATCTGATCCTGCATTCAAAGTCATTCCTCTCTGGCTACTTCACTCTGCACATG
     1261 ────┼──────────┼──────────┼──────────┼──────────┼──────────┼ 1320
              TCTTTGGTAGACTAGGACGTAAGTTTCAGTAAGGAGAGACCGATGAAGTGAGACGTGTAC b    E  T  I  *  S  C  I  Q  S  H  S  S  L  A  T  S  L  C  T  *   -
                             B                B  M            H
                    D     RSD E  s            sM b            iT
                    d     scd a  m            as o            nf
                    e     aoe r  A            Wp |            fi
                    |     ||| || |            || |            ||
                                /
              AGAGATGCTCAGACTGTATCAAGTACTCAGAAAGAAGAGACTACCGGACACTCCTGAATC
     1321 ────┼──────────┼──────────┼──────────┼──────────┼──────────┼ 1380
              TCTCTACGAGTCTGACATAGTTCATGAGTCTTTCTTCTCTGATGGCCTGTGAGGACTTAG b    E  M  L  R  L  Y  Q  V  L  R  K  K  R  L  P  D  T  P  E  S   -
           B
           s
           pN                              T
     C     ||              D  S            a
     Av   4aR    D         r  Aa           q             A
     li   01s    r  B      Ba vu           |             P
     uJ   7la    d  c      s| a9           |             o
     ||   |||    | |       r| 16           -             I
                                           2
       /                         /
              CAGCTCATGTACAGAACCATCTGAAACACCCAGTGGACCACAATGCTCTGTGGTATGTGA
     1381 ────┼──────────┼──────────┼──────────┼──────────┼──────────┼ 1440
              GTCGAGTACATGTCTTGGTAGACTTTGTGGGTCACCTGGTGTTACGAGACACCATACACT
```

S               BMT
         T           a               sas                           T
         s   Tu  D   tep             H       M   A   s
         p   a3  p   E14             p       n   p   p
         E   qA  n   I15             h       I   o   E
         I   II  I   III             I       I   I   I
                                     /
        ATTTCGATCATCATAGAAGGTGACCCCTCTCTATGTAGAATTTTTATTTTTCAAGCAAAT
1441   ----+----+----+----+----+----+  1500
        TAAAGCTAGTAGTATCTTCCACTGGGGAGAGATACATCTTAAAAATAAAAAGTTCGTTTA b    F   R   S   S   *   K   V   T   P   L   Y   V   E   F   L   F   F   K   Q   I   -

T
             l
             h
             1           M T
             1           a s                               T
             1   M       e p           M A   s     S M
             1   n       I 4           s p   p     f s
             I   I       I 5           e o   E     c I
             I   I       I I           I I   I     I I
        ACTTATGACCTCATCAAAGAAAATAATGTCACTTGTTAAATTCACTGTAGTGATACATAA
1501   ----+----+----+----+----+----+  1560
        TGAATACTGGAGTAGTTTCTTTTATTACAGTGAACAATTTAAGTGACATCACTATGTATT b    L   M   T   S   S   K   K   I   M   S   L   V   K   F   T   V   V   I   H   K   -

T
                              tM T
                              ho s
                         MH   B1eMp        S             B
                         np   sLIn4        f             s
                         lh   rlI15        c             r
                         II   IIIII        I             I
                              / /
        AGTAAATGCTACCTCTGACCTCTGACCCAGTCACCTTCTGTAGAGAGTTCCAGTCCTTTT
1561   ----+----+----+----+----+----+  1620
        TCATTTACGATGGAGACTGGAGACTGGGTCAGTGGAAGACATCTCTCAAGGTCAGGAAAA
```

B                 MH                M     B  M
            c                 sp                m     f  s
            c                 eh                e     a  e
            I                 II                I     I  I
      GTGATGGAATACATCATTTCCAACTTAAAACTTTCACCTTGAAGTTATGGTCTAGTTAAG
1621  ————————+————————+————————+————————+————————+————————+  1680
      CACTACCTTATGTAGTAAAGGTTGAATTTTGAAAGTGGAACTTCAATACCAGATCAATTC b     *  W  N  T  S  F  P  T  *  N  F  H  L  E  V  M  V  *  L  R    -

B              T
               s              l
               p              h
               N1             1                  M           M
           B   12         B M 1                  b     B     b
           a   a8         s n 1                  o     b     o
           n   I6         I I I                  I     s     I
           I   VI         I I I                  I     I     I
      ACATCAGGGGCACCTCCGTTTCTTGGTTTTGTATTGTTTGAAAGAAGACGACATCTTCCT
1681  ————————+————————+————————+————————+————————+————————+  1740
      TGTAGTCCCCGTGGAGGCAAAGAACCAAAACATAACAAACTTTCTTCTGCTGTAGAAGGA b     H  Q  G  H  L  R  F  L  V  L  Y  C  L  K  E  D  D  I  F  L    -

B                                          H
      p      C                                   i        C
      u D    A v M                               n  S  v  P
      l d    l  i n                              c  f  i  s
      O e    u J l                               I  c R  t
      I I    I I I                               I  I I  I
       /  /
      CCTTAGCTGTGTGTTGAAAATGAAAGGGATTGAAAGCACAGTGTCAACTGCAGAATGGTT
1741  ————————+————————+————————+————————+————————+————————+  1800
      GGAATCGACACACAACTTTTACTTTCCCTAACTTTCGTGTCACAGTTGACGTCTTACCAA
```

H                    R                          C
     i T                  T l              M         v
     n f                  a e              n         i
     f i                  q A              l         J
     l l                  l l              l         l
                /
     GATTCTCACTCTGAAAGGATTTACTTCGAGTTATAATGTGGGGGTTAGGAGAGGGGCTGT
1801 ————————+————————+————————+————————+————————+————————+ 1860
     CTAAGAGTGAGACTTTCCTAAATGAAGCTCAATATTACACCCCCAATCCTCTCCCCGACA b    I  L  T  L  K  G  F  T  S  S  Y  N  V  G  V  R  R  G  A  V    -

N                                BMT
                       l                                s a s
        T              a     D        M         H       l e p    B
        S              l     d        n         p       E I 4    s
        p              l     e        l         h       I I 5    r
        E              l     l        l         l       I I I    l
                                                                /
     TTTTTCCTAATTCCCACCATGTCCTCTAAGTGTTCACAAGGTCAAGTTCAGAAGGTCACC
1861 ————————+————————+————————+————————+————————+————————+ 1920
     AAAAAGGATTAAGGGTGGTACAGGAGATTCACAAGTGTTCCAGTTCAAGTCTTCCAGTGG b    F  S  *  F  P  P  C  P  L  S  V  H  K  V  K  F  R  R  S  P    -

T
        D        a  N
        r        q  l                          C        T M
        a        l  a        D                 v    A   s b            E
        l        l  l        d                 i    p   p o             a
        l        -  l        e                 J    o   E l             r
        l        2  l        l                 l    l   l l             l
     CAGTGAGTTCATCATGCTATCATTCTGAGCAGGAAGCCAAGAATTTCGCTCTCTTCATTT
1921 ————————+————————+————————+————————+————————+————————+ 1980
     GTCACTCAAGTAGTACGATAGTAAGACTCGTCCTTCGGTTCTTAAAGCGAGAGAAGTAAA
```

FIG.11K

```
b    S  E  F  I  M  L  S  F  *  A  G  S  Q  E  F  R  S  L  H  F   -
                    T           C C              S
              B     s           v a              f
              s     p           i c              o
              g     E           R 8              N
              I     I           I I              I
         TTTTCAGTAATTTCTCCACACTGCACGCTCTTTTGTATTATTTTCCCTGATGCCTTATGA
    1981 ─────────┼─────────┼─────────┼─────────┼─────────┼─────────┼ 2040
         AAAAGTCATTAAAGAGGTGTGACGTGCGAGAAAACATAATAAAAGGGACTACGGAATACT b    F  Q  *  F  L  H  T  A  R  S  F  V  L  F  S  L  M  P  Y  E   -

T
                                t
              N S               h
              I a               ETl
              BaDu           B  Acs1
              clp3           c  pop1
              IInA           c  oREI
              IIII           I  IIII
                   /              /
         AACAGCATGATCAAACAACAGATGGAATTC
    2041 ─────────┼─────────┼─────────┼ 2070
         TTGTCGTACTAGTTTGTTGTCTACCTTAAG b    T  A  *  S  N  N  R  W  N   -
```

Enzymes that do cut:

| | | | | | | | |
|---|---|---|---|---|---|---|---|
| AciI | AflIII | AluI | AlwI | AlwNI | ApaBI | ApoI | AvaI |
| AvaII | BamHI | BanI | BanII | BbsI | BbvI | BccI | Bce83I |
| BcefI | BclI | BfaI | BpmI | Bpu10I | Bpu1102I | BsaI | BsaAI |
| BsaBI | BsaHI | BsaJI | BsaWI | BsgI | BsiEI | BsII | BsmI |
| BsmAI | Bsp1286I | Bsp1407I | BspGI | BspMI | BspWI | BsrI | BsrFI |
| BstEII | BstXI | BstYI | Cac8I | CviJI | CviRI | DdeI | DpnI |
| DraIII | DrdI | DsaI | EarI | Eco47III | Eco57I | EcoRI | EcoRII |
| FauI | Fnu4HI | FokI | FspI | HaeII | HaeIII | HgaI | HgiEII |
| HhaI | HincII | HindIII | HinfI | HphI | MaeII | MaeIII | MboII |
| MlyI | MmeI | MnlI | MseI | MsII | MspI | NciI | NcoI |
| NlaIII | NlaIV | NspI | NspBII | PflMI | PleI | PstI | PvuI |
| PvuII | RleAI | RsaI | Sau96I | Sau3AI | ScaI | ScrFI | SfaNI |
| SfcI | SphI | StyI | TaqI | TaqII-1 | TaqII-2 | TfiI | Tsp45I |
| TspEI | Tth111I | Tth111II | XcmI | XhoI | | | |

FIG. 11L

Enzymes that do not cut:

| | | | | | | | |
|---|---|---|---|---|---|---|---|
| AatII | AccI | AflIII | AgeI | ApaI | ApaLI | AscI | AseI |
| AvrII | BaeI | BcgI | BcgI | BglI | BglII | BscGI | BsiI |
| BspEI | BspHI | BsrBI | BssHII | Bst1107I | Bsu36I | ClaI | DraI |
| DrdI | EaeI | EagI | Eam1105I | EciI | EcoNI | EcoO109I | EcoRV |
| Esp3I | FinI | FseI | GdiII | HaeI | HgiAI | HpaI | KpnI |
| MluI | MscI | MunI | NaeI | NarI | NdeI | NheI | NotI |
| NruI | NsiI | NspV | PacI | PflI108I | PmeI | PmlI | PshAI |
| Psp5II | Psp1406I | RsrII | SacI | SacII | SalI | SapI | SfiI |
| SgrAI | SmaI | SnaBI | SpeI | SrfI | Sse8387I | SspI | StuI |
| SunI | SwaI | ThaI | XbaI | XmnI | | | |

FIG. 11M

MU-SUBTYPE OPIOID RECEPTOR

The present application is a continuation of U.S. Ser. No. 08/075,447, filed Jun. 11, 1993, now abandoned, which was a continuation-in-part of U.S. Ser. No. 08/026,140, filed Feb. 26, 1993, now abandoned, which is a continuation-in-part of U.S. Ser. No. 07/855,286, filed Mar. 23, 1992 which is now abandoned, the contents which are incorporated herein by reference.

FIELD OF THE INVENTION

The present invention relates to substantially pure opioid receptors.

BACKGROUND OF THE INVENTION

Opioids are a chemically diverse group of compounds which includes naturally occurring peptides and alkaloids as well as a large number of synthetic analogs. The physiological effects of opioid agonists include analgesia, drowsiness, changes in mood, respiratory depression, decreased gastrointestinal motility, nausea, vomiting and alterations in the endocrine and autonomic nervous systems (Jaffe and Martin, in The Pharmacological Basis of Therapeutics, Gilman, A. G. et al., eds.; MacMillan, New York, pages 491–531, 1985).

Opioid Subtypes and Their Receptors

The physiological actions of opioids are mediated through specific receptors that exist in the responsive tissues. In vitro characterization of these receptors by binding of radiolabelled opioid alkaloids to brain membranes was first described in 1973 by three independent groups of investigators was used to search for endogenous opioids in vertebrate brain. This search led to the discovery of met- and leu-enkephalin, two opioid pentapeptides, in 1975. In that same year, other opioid peptides (derived from the gene later designated as "POMC") were discovered in the pituitary. Selective binding of the different peptide and nonpeptide opioids to the receptors in membranes derived from different tissues and brain regions plus correlations with pharmacological selectivities of the opioid drugs established the existence of opioid receptor subclasses (history reviewed by A. Goldstein in Opioids: Past, Present and Future, Collier, H. O. J. et al., eds.; Taylor and Frances Ltd., London, 1984, pages 127–143).

The best characterized classes of opiate receptors are the mu ($\mu$), delta ($\delta$) and kappa ($\kappa$) classes, based on clear differences in their ligand selectivities and pharmacological effects (Lord et al., Nature, 267:495–499, 1977). Sigma ($\sigma$) (Jaffe and Martin, supra), and epsilon $\epsilon$ (Schulz et al., J. Pharmacol. Exp. Ther. 216:604–606, 1981) are also thought to exist, based on differential pharmacology and ligand binding. There is also evidence for receptor subtypes within these major classes (Jaffe and Martin, supra).

Mechanisms of Action of Opioids

The best characterized effects of opioids on cell metabolism are decreased $Ca^{2+}$ conductance, increased $K^+$ conductance and decreased levels of cAMP (Loh and Smith, Ann. Rev. Pharmacol. Toxicol., 30:123–147, 1990). These functions are among those known to be regulated by the receptor-associated G proteins, which also confer high-affinity ligand binding on the receptors they associate with (Birnbaumer et al., Biochem. Biophys. Acta. 1031:163–224, 1990). In fact, both the binding of opiate agonists and their effects on adenylate cyclase have been shown to be GTP-dependent. It is likely that a thorough understanding of the signaling mechanisms of opiate receptors, including the identification of specific, receptor-associated G proteins, would shed light on underlying the mechanisms of functions such as analgesia and addiction.

Numerous previous attempts have been made to isolate opioid receptors. Bidlack et al. (PNAS U.S.A. 78:636–639, 1981) disclose the isolation of three species in the molecular weight range of 25–50,000 daltons, isolated from rat brain using affinity chromatography with 14-β-bromoacetamido-morphine. Gioannini et al. (J. Biol. Chem. 260:15117–15121, 1985) describe the isolation of a 65,000 MW protein from bovine striatum using affinity chromatography with β-naltrexylethylenediamine. Maneckjee et al. PNAS U.S.A. 82:594–598, 1985) disclose three proteins having MWs of 92,000, 42,000 and 35,000, which were identified from rat brain using affinity chromatography with "Hybromet" a $\mu$-selective ligand. Cho et al. (PNAS U.S.A. 83:4138–4142, 1986) and Ueda et al. (Neurosci. Lett. 75:339–344, 1987) both teach the isolation of a 58,000 molecular weight species from rat brain by affinity chromatography with 6-succinyl morphine as ligand. The peptide described by Cho et al. has subsequently been shown not to be a transmembrane spanning protein (Schofield et al., EMBO J. 8:489–495, 1989). Simon et al. (Neuropeptides 10:19–28, 1987) describe the isolation of 65,000 and 58,000 MW peptides from frog brain by affinity chromatography with the opioid peptide DADLE. Ahmed et al. disclose a 66,000 MW species which was isolated from human placenta by binding to thiol-sepharose, followed by gel electrophoresis, and binding to wheat germ agglutinin-agarose. Notwithstanding these many reports, however, none of these species has ever been verified as an opioid receptor, nor has any of them ever been reported to yield either amino acid or nucleotide sequence which was verifiable as encoding a functional receptor. The logical inference is that the "receptors" allegedly purified in these papers were either not adequately pure to permit sequencing, or are not in fact the receptors they were believed to be. A need therefore continues to exist for a verifiable isolated opioid receptor sufficiently pure to allow sequence to be determined. The invention described in the present application now fulfills such a need.

SUMMARY OF THE INVENTION

The present invention relates to a substantially pure opioid receptor protein, and biologically active fragments thereof. In addition the invention relates to the nucleotide sequence encodes that for the opioid receptor. The term "substantially pure" as used throughout the present specification and claims, means a protein free of other non-opioid receptor cellular proteins with which it would normally be associated in its membrane-bound state. Such a protein is essential in order to successfully obtain accurate sequence information. A purified opioid receptor is isolatable by binding a biotinylated opioid ligand with membranes derived from an appropriate tissue source, i.e., one expected to express opioid receptors, to form a receptor:ligand complex. The membranes are then solubilized in a bile-salt like detergent composition, and contacted with an avidin or streptavidin containing affinity substrate, to which the biotinylated receptor:ligand complex will bind. The receptor is eluted from the bound complex by contact with an eluant containing GTP and NaCl or NaCl alone. The eluate is then contacted with a lectin affinity column which specifically binds glycoproteins.

In one embodiment, a receptor is identified by its binding a β-endorphin ligand. In particular, three species are identifiable by this characteristic in the method described. A primary species has a molecular weight of about 66,000, while two minor species have molecular weights of 140–160,000 and 50–55,000. Based on the affinity for β-endorphin, and other pharmacological data, these species are believed to represent a μ opioid receptor type.

In addition to its use in sequencing and ultimate cloning of the receptor gene, the purified receptor, or biologically active fragments thereof, can be used in production of monoclonal or polyclonal anti-receptor antibodies and to identify patterns of post translational modifications and to Elucidate associated G. proteins. "Biologically active" in the present context refers not only to fragments which retain ligand binding activity, but also refers to fragments capable of raising an antibody response when injected into a host animal. Such antibodies (poly- or monoclonal) can be used in manipulation. of peripheral opioid receptors involved in gut motility and growth hormone secretion. Such antibodies can also be utilized in drug delivery to specific tissues or for tumor imaging.

Receptor clones isolated utilizing sequence information obtained from the purified protein are useful in identifying other receptor subtypes, in screening for new opioid ligands, and for understanding mechanisms of opioid action, for example, drug addiction.

BRIEF DESCRIPTION OF THE FIGURES

FIG. 9. Amino acid sequence of the rat brain ξ-opiate receptor SEQ ID NO:5 predicted from the sequence of the cDNA RC8-I, and comparisons of sequence of other G-linked receptor family members. RC8-1 is subject to double stranded sequencing by automated and manual means, and the translation product open reading frame SEQ ID NO:2 aligned with those of the mouse δ-opioid receptor (DOR-1 SEQ ID NO:6), rat somatostain receptor (SOMAT SEQ ID NO:7), human N-formyl-methlonine receptor (F-PEP SEQ ID NO:8), human opioid hinding protein (OPB-R SEQ ID NO:9), rat neuromedin K recptor (NEU-K SEQ ID NO:10), rat rhodopsin (RHODOP SEQ ID NO:11), and rat beta2 adrenergic receptors (B-2ADR SEQ ID NO:12).

FIG. 10. Saturation analyses of binding of [3H]DAMGO (top) and [3H]DADLE (bottom) of membranes prepared from COS cells transfected three days before out with 100 nM naloxone added to parallel incubations to estimate nonspecific binding.

FIG. 11. Nucleotide Sequence of μ receptor and predicted amino acid sequence of μ opiate receptor C-DNA, SEQ ID NO:1 open reading frame analyzed for plasmid cDNA.

Figure 1A:
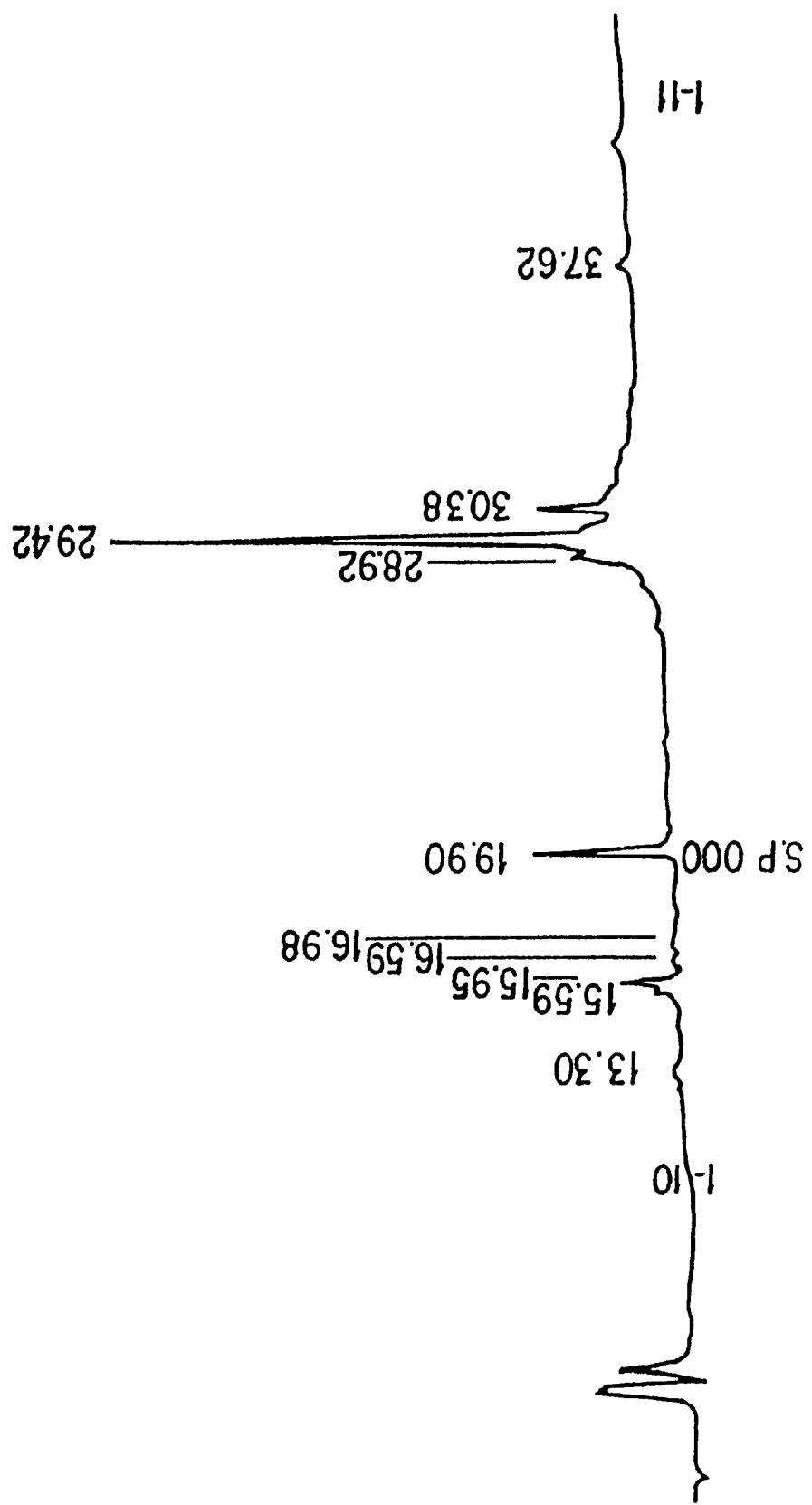
FIGS. 1A–1B. Purification of Biotinylated β-Endorphin. A. Analytical HPLC of crude biotinyl β-endorphin. B. Preparative HPLC of biotinylated β-endorphin.

B. RNase protection and phosphiomager autoradiogram of a 400 basepair fragment protected from digestion by 5 μg of μ-opiate receptor mRNA extracted from: (l-r) lane 1: cerebral cortex; lane 2: straitum: lane 3: thalamu; lane 4; hypothalamus; lane 5: midbrain; lane 6: hippocampus; lane 7: brainstorm; lane 8: cerebellum; lane 9: cervical spinal cord; lane 10; liver. C & D Photomicrographs of emulsion autoradiograms of in situ hybridization grain densities overlaying thalamic (C) and lateral habcnula, medial aspect (D) neurons expressing μOR mRNA in a representative section through rat diencephalon ( ). Similar results are obtained in experiments using tow distinct μOR mRNA hybridization probes, and in sections from three different brains. Objective magnification=100×(C), and 4×(D).

DETAILED DESCRIPTION OF THE INVENTION

The purified-opioid receptors are isolated by a receptor purification method disclosed in U.S. Ser. No. 07/677,003, now U.S. Pat. No. 5,225,543, issued Jul. 6, 1993 the contents of which are incorporated herein by reference. The purified opioid receptors are described in U.S. Ser. No. 08/026,140 the contents which are incorporated herein by reference. Opioid receptors can be found in a wide variety of tissue types (Jaffe and Martin, supra, the contents of which is incorporated herein by reference). In particular, the δ, μ, κ, and σ classes of receptors are found in brain, as well as other tissues; the ε type is found in vas deferens and the κ type is also plentiful in placenta (Ahmed et al., supra).

The opiate receptor is isolated initially as a complex with its associated G proteins. A number of opiate or opioid analogs are commercially available that can be used for receptor binding. For example, Research Biochemicals, Incorporated, 1991 Catalog, page XV, identifies a number of opioid ligands by their subtype specificity. The ligand used will generally be selected based on its affinity for a particular receptor subtype. In a preferred method for purification, a biotinylated opiate analog is used. In the following examples, the ligand used for isolation of receptor is a biotinylated β-endorphin. In the preferred isolation method, the ligand is first bound to intact cell membranes, thereby forming a receptor:ligand (R:L) complex. After this prebinding step, the membranes are solubilized in detergent and intact receptor:ligand complexes are obtained. A useful detergent for this purpose is a combination of deoxycholate and lysophosphatidylcholine in a 1:1 ratio, preferably at a concentration of 0.2% w/v or less. At this stage, the complex consists of the receptor and its associated G protein subunits. The association of the receptor with G proteins is confirmed by the rapid dissociation of the complex in the presence of a stable GTP analog.

The solubilized complex is then contacted with an appropriate high affinity binding column. When the ligand is biotinylated, the column used is preferably streptavidin-agarose (SA-A), whereby the biotinylated portion of the R:L complex will tightly bind to the streptavidin. Streptavidin is preferred, due to its lower non-specific binding; however, free and its lower non-specific binding; however, free and immobilized avidin is also available (Pierce, Vector) and may be suitable for some purposes. The column is eluted with a GTP analog, such as GTP-γ-S. The GTP analog serves to dissociate G protein subunits from the receptor, thereby lowering the affinity of the receptor for its ligand, and thus indirectly causing dissociation from the ligand. In a preferred embodiment, the elution with GTP analog is combined with elution with at least 25 mM NaCl, preferably 50–100 mM, up to a maximum of about 500 mM NaCl. Although dissociation will occur with GTP alone, it occurs at a relatively low level (about 30%), and the use of NaCl enhances this dissociation. Alternately, a high level, i.e., 500 mM of salt can be used alone. The eluate from the streptavidin column is then incubated with a lectin affinity chromatography substrate, such as wheat germ agluttinin (WGA)-agarose, which will separate glycoproteins from nonglycoproteins. The eluate containing the glycosylated material shows a protein with a molecular weight of about 66,000; this protein is also seen in material eluted by GTP-γ-S and/or with NaCl, but is not seen in eluates from samples not previously bound with the biotinylated β-endorphin, indicating its ligand dependence. This band appears to represent an opioid receptor, presumably a "mu" or "delta" type opioid receptor, based on β-endorphin's known preferential binding to "mu" or "delta" receptor types, and the pharmacological data discussed below.

Figure 4:
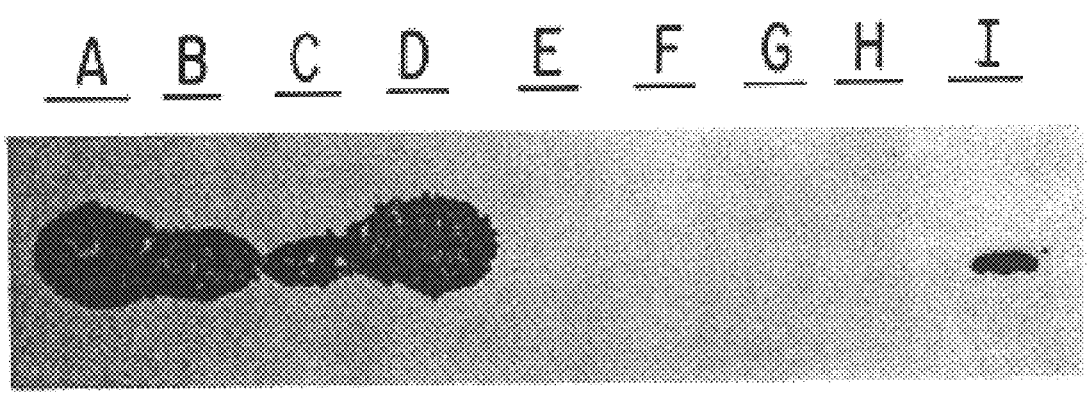
FIG. 4. Immunoreactivity of 30–40,000 MW Material Eluted by GTP from Streptavidin-Agarose Previously Incubated with R:L Complexes Made with Biotinylated Somatostatin or β-Endorphin. WGA-A nonbound fractions of GTP eluates from streptavidin from receptor purifications done with biotinyl-somatostatin 28 (bio-S28) or biotinyl-β-endorphin are separated by SDS-PAGE and analyzed by Western blotting. The electroblotted samples are first reacted with an anti-$G_{i\alpha}$ rabbit antiserum (1:400 dilution). The second antibody is a peroxidase-coupled, donkey antirabbit Ig antiserum (1:104 dilution). The final complex is antiserum (1:104 dilution). The final complex is detected by enhanced chemiluminscence (ECL; Whitehead, T. P. et al., Nature 305:158–159, 1983). ECL is based on the peroxidase-catalyzed oxidation of luminol and subsequence enhanced chemiluminescence where the probe is bound (Amersham Life Science Products catalog, 1989/90 edition, page 5). Lanes A–C contain 200, 100 and 50 ng of recombinant $G_{i\alpha2}$. Lanes D and E are from a purification of SRIF receptor by the method of Eppler et al. (as described in U.S. Ser. No. 07/677,003) with 20 nM bio-s28, Lane E, binding step done with 20 nM bio-S28+20 μM S14. Lanes F–I are from a purification of opioid receptor by the method described herein. F and G are eluates with 500 MM NaCl. H and I are eluates with 100 pM GTP-g-S. F and H are from a sample without ligand in the binding step. G and I are from a sample with 100 nM biotinyl-β-endorphin in the binding step.

In the nonglycosylated material that is not bound to the lectin affinity column, there appears a second smaller band of about 30–40,000, which apparently elutes with GTP-gamma-S alone (i.e., without NaCl). This material also is apparently ligand-dependent, since, like the 66K band, it only appears in eluates from samples which have been prebound with biotinyl-β-endorphin. It is assumed that this band represents G protein subunits, particularly in light of binding with anti-$G_{i\alpha}$ as seen in FIG. 4.

The identity of the isolated material is confirmed by additional experiments using nonbiotinylated β-endorphin analog ligands. A [$^{125}$I]β-endorphin analog is used as described above to create R:L complexes in rat brain cell membranes. These complexes, when applied to wheat germ agluttinin, and eluted with N-N'-N"-triacetyl-chitotriose, shows a fairly high level of specifically bound material (see Tables 1 and 2, infra), confirming the identity as a glycoprotein.

The purified 66 kDa glycoprotein is subjected to Lys-C endoprotease digestion, SDS polyacrylamide gel electrophoresis and electroblotting, producing a 15 kDa peptide band. This peptide yields 20 cycles of high quality amino acid sequence. The N-terminus of this band overlaps by 4 amino acid residues with a 7-amino acid residue sequence obtained from a band of about 3 kDa from a cyanogen bromide digest, giving a total sequence length of 23 amino acid residues. The sequence (Sequence ID NO.14) obtained is as follows:

Lys-Glu-Lys-Asp-Arg-
 Asn-Leu-Arg-Arg-Ile-Thr-Arg-Met-Val-Leu-Val-Val-Val-<u>Ala</u>-
 <u>Val</u>-Phe-<u>Ile</u>-Val

This sequence is quite similar to a region of the SSTR1 somatostatin receptor, spanning parts of intracellular loop III and transmembrane region VI. Significantly, it is 83% identical with the same region of a recently cloned delta opioid receptor from mouse (C. J. Evans, et al., Science 258:1952–1955, 1992). Underlined residues indicate the differences between the two receptors in this region.

Pharmacological evaluation of the purified protein indicates that it is a mu-subtype receptor, and that the difference between the repacted delta subtype receptor and the present receptor is not attributable to a simple species difference, but is due to a known mu-specific peptide capable of blocking the binding of β-endorphin to the isolated receptor.

The novel sequence information obtained provides the basis for isolation and cloning of the corresponding gene encoding the receptor. The delta opioid sequence in this region is nearly identical to the same region of SSTR1, and seems to be highly conserved in a set of 5 or 6 receptors, indicating homology in the mu receptor as well. The combination of primers, including the mu specific-based primer, in PCR of whole brain mRNA, selectively yields the mu receptor.

The purified receptor, or biologically active fragments thereof, are useful for a number of purposes. For example, the purified material, in glycosylated or nonglycosylated form, is used to create monoclonal or polyclonal antibodies having specificity for the opioid receptor. The technology for creation of monoclonal antibodies is well known in the art (see, e.g., Goding, Monoclonal Antibodies: Principle and Practice, 2nd Ed., 1986). Such antibodies have utility in manipulating purified opioid receptors involved in gut motility and growth hormone secretion, or in drug delivery to specific tissues or for tumor imaging. General techniques for preparing anti-receptor antibodies are found in U.S. Pat. No. 4,857,637, the contents of which are incorporated herein by reference.

The isolated receptor protein itself, and protein expressed from the cloned opiate receptor cDNA is useful in screening assays to identify compounds that act as analogs. For example, the receptor protein is immobilized by any means which does not interfere with opiate binding activity. The immobilized receptor is then contacted with a specific compound or mixture and its ability to compete with radiolabelled opiate for binding to the receptor is evaluated. Variations on this method are apparent to those skilled in the art.

The present invention encompasses the opiate receptor protein and its biologically active fragments produced by any means, whether synthetically, recombinantly, or by purification of the native protein. The isolated opiate receptor, as described above, is used in protein sequencing procedures. The protein sequence in turn is used to design oligonucleotide probes used to screen λgt10 libraries containing the relevant cDNA (copies of RNA), e.g., from brain cells. Hybridization of oligos with the library identifies the clone(s) containing the SRIF receptor gene or portions thereof. The gene or gene fragments are isolated from the clones, the whole gene reconstructed and then ligated into an appropriate vector by known methods. The vector is chosen based upon the choice of preferred host cell. The host cell is prokaryotic, e.g., E. coli or other bacteria; or eukaryotic, e.g., yeast, insect, or mammalian cells.

The following non-limiting examples further illustrate the present invention.

EXAMPLES

I. Experimental Procedures

The following materials and methods are referred to throughout the Examples.

1. Preparation of Rat Brain Membranes

Whole male rat brains frozen in liquid $N_2$ are purchased from Pel-Freez (Rogers, Ark.). All procedures for membrane preparation are carried out at a temperature of 2–6° C. The brains are homogenized in a Waring blender in a buffer containing 1 mM Na-bicarbonate (pH 7.2), 1 mM EDTA, 1 mM EGTA (all chemicals from Sigma Chemical, St. Louis, Mo.) and 0.7% (vol./vol.) of the 100×4Pase protease inhibitor mixture (see "Protease Inhibitors" below). The ratio of tissue/homogenization medium is from 25–35 gm of brain/500 ml. The blender is controlled through a variable output rheostat (Staco Energy Products, Dayton, Ohio; type 3PN1010) at a setting of 40. The homogenate is centrifuged for 10 minutes at 1,000×g pellet is rehomeginized in 500 ml of homogenization medium and recentrifuged for 10 minutes at 1,000×g. The 1,000×g pellet is discarded. The 1,000×g supernatants are combined and centrifuged for 30 minutes at 20,000×g. The 20,000×g membrane pellet is washed by being resuspended with a Dounce homogenizer in 500 ml of homogenization medium supplemented with 10 mM EDTA (pH readjusted to 7.4) and then washed twice by being resuspended in 25 mM Tris buffer (Sigma Chemical Co.; pH 7.4) and centrifuged for 25 minutes at 20,000×g. The final membrane pellet is resuspended in 25 mM inhibitor mixture to a protein concentration of 4–12 mg/ml. The resuspended membranes are aliquoted, frozen on dry ice and stored at –90° C.

2. Receptor Binding Methods

Binding of [$^{125}$I]-labelled β-endorphin, β-endorphin and other β-endorphin analogs and opioids is done in a binding buffer containing 50 mM HEPES (Sigma; pH 7.4; pHed with KOH), 0.1% (w/v) bovine serum albumin (Miles Laboratories, Elkhart, Ind.) and protease inhibitors as specified below for specific applications. All binding incubations are carried out at room temperature (20–23° C.).

A. Analytical—This assay is carried out in 96 well microtiter plates (Immulon II with snap-off wells; Dynatech, Chantille, Va.). To carry out the assay, the following components are added to the wells in the order and volumes shown: (1) 5 μl of non-labelled ligand. For this purpose, ligands (for example β-endorphin or biotinylated b-endorphin) are made up at 40× the desired final concentration in the 40×P/B/Pz protease inhibitor mixture (Experimental Procedures. 4.C.) (2) 50 μl of [$^{125}$I]β-endorphin in binding buffer+1/100 volume of the 100×4Pase protease inhibitor mixture; mix briefly on a microtiter plate shaker (Dynatech Micro-Shaker II, Dynatech, Chantilly, Va.). (3) 145 μl of rat brain membrane diluted in binding buffer+1/1000 volume of 100×4Pase to deliver 30–50 μg of membrane protein per well. The plates are then covered with Linbro Mylar plate sealers (Flow Labs, McLean, Va.) and incubated for 1 hour at room temperature (20–23° C.). The membranes are pelleted by centrifugation at 2,000×g, the supernatants (containing nonbound ligands) are decanted and the pellets are washed by the addition of 200 μl of ice cold binding buffer, brief shaking and recentrifugation. CPM of [$^{125}$I] in the final membrane pellets is then counted in a gamma counter (LKB Gammamaster 1277; 80% efficiency).

B. Preparative—Rat brain membranes are diluted to a concentration of 0.5 mg of membrane protein/ml in binding buffer containing 1/400 (vol./vol.) of the 400×P/B/Bz protease inhibitor mixture (see Section 4). Biotinyl-β-endorphin (synthesized and purified as described below; 1:1 mixture of HPLC fractions 1 and 2 is added, most commonly to a concentration of 60 nM. The mixture is incubated either by stirring in a large polypropylene beaker (1–2 liters volume)

or by rotation on a tube rotator (100–250 ml per polypropylene centrifuge tube). Control incubations designed to show ligand specificity of purified proteins are done by various means as follows: i. No ligand. Rat brain membranes are incubated as above except with no biotinyl-β-endorphin or other opioid analog. ii. Blocking ligand. Binding of biotinyl-β-endorphin is blocked by a large molar excess (500–1,000 fold) of a non-biotinylated opioid ligand such as β-endorphin, met-enkephalin or nalox-one. In this case, the blocking ligand is added from 5–15 minutes prior to the addition of biotinyl-β-endorphin. In some cases only the blocking ligand is added. For example, the receptor sites may simply be saturated with naloxone. The binding reactions (1 hour) are terminated by centrifugation for 10–15 minutes at 20,000×g. The supernatants are decanted and the membrane pellets are washed with a volume of binding buffer (minus bovine serum albumin) equal to the original incubation volume. For this wash step, the membranes are dispersed in the wash buffer in a Dounce homogenizer, diluted out in the wash buffer and recentrifuged at 20,000×g. This final membrane pellet is then solubilized in detergent as described in part 3, below, and used to characterize soluble R:L complex (when prebinding is done with $[^{125}I]$β-endorphin) or for purification of opioid receptor and associated G protein (when prebinding is done with biotinyl-β-endorphin).

3. Solubilization of B-Endorphin:Opioid Receptor Complexes (R:L Complexes)

This step is carried out in a solubilization buffer containing 25 mM Tris (pH 8.0) and 10% glycerol. All procedures are at 4° C. or on ice. Deoxycholate:lysophosphatidylcholine (1:1 (w/w) mixture; hereafter referred to as D:L; stock solutions=10% (w/v) in $H_2O$; purchased from Sigma] is added to the solubilization buffer to a final concentration of 0.15% w/v (deoxycholate=0.075%; lysophosphatidylcholines=0.075%). Protease inhibitors (100×4Pase; 1% vol./vol.) are added and rat brain membranes are diluted out into this medium to a protein concentration of 0.5 mg/ml. After 30–45 minutes incubation on ice, the samples are centrifuged for 30 minutes at 100,000× g. The 100,000×g supernatants are aspirated out of the centrifuge tubes as far as possible without disturbing the pellets of insoluble material. Then the remaining supernatant is poured out of the tubes and filtered through a 0.2μ cellulose acetate or nylon filter unit (Corning Inc., Corning, N.Y.) to remove particulate matter dislodged from the pellet. This filtered supernatant is then combined with the material removed by aspiration.

4. Protease Inhibitors

Three mixtures of protease inhibitors are used in these procedures. (A) 100×4Pase. 5 mg pepstatin A, 15 mg chymostatin, 38 mg leupeptin and 73 mg phenylmethylsulfonylfluoride (PMSF; all compounds from Bachem, Torrance, Calif.) are dissolved per 5 ml of dimethylsulfoxide (DMSO; Aldrich Chemicals). Aliquots are stored frozen at 4° C. (B) 40×PMSF/Baci. 2 mg of PMSF and 2 mg of bacitracin (Sigma) are dissolved per ml of DMSO. Aliquots are stored frozen. C. 400×P/B/Bz. 20 mg of PMSF, 20 mg of bacitracin and 20 mg of benzamidine (Sigma) are dissolved per ml of DMSO. Aliquots are stored frozen.

5. Synthesis and Purification of Biotinyl-β-Endorphin

A peptide with the amino acid sequence $H_2$N-Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-Tyr-Lys-Lys-Gly-Glu--[biotinyl-Lys$^{32}$]-CO ([biotinyl-Lys$^{32}$]β-endorphin) (Sequence ID No. 13) is synthesized at Applied Biosystems Inc. (ABI; Foster City, Calif.). Synthesis is by solid phase from the C terminal by the Fmoc method. After synthesis, while the peptide is still on the resin, the ε-amino group of Lys$^{32}$ is specifically deprotected. The ε-amino group is then reacted with N-hydroxy-succinimidyl-aminohexanoyl-biotin (NHS-LC-Biotin; Pierce, Rockford, Ill.; "LC"=aminohexanoate). After biotinylation, all of the protected amino acid residues are deprotected and the peptide is released from the resin by HF cleavage. In the example shown the final product (about 50% pure; see FIG. 1A), is further purified by reverse phase HPLC on a Brownlee "Aquapore" C8 column (1×25 cm). Elution is by a gradient of acetonitrile mixed in water/0.1% trifluoroacetic acid. Two closely spaced product peaks are eluted from the column. These two peptide fractions are lyophilized and solubilized in water at 1 mg/ml. Aliquots are stored frozen at −90° C.

6. Purification of Opioid Receptor 100,000×g supernatants from rat brain membranes carried through the ligand binding and solubilization steps are incubated with immobilized streptavidin (streptavidin-agarose or SA-A; Pierce Chemical, Rockford, Ill.). The incubations contain 1 volume of SA-A per 29 volumes of supernatant. Incubations are for 4 hours at 4–8° C. on a tube rotator. Then the mixtures are poured into glass chromatography columns (Econo-Columns, Bio Rad Labs, Richmond, Calif.) and the non-bound material is filtered through the bed on packed resin. The resin is washed with 20 bed volumes of solubilization buffer+0.15% D:L+1/500 volume of the 100×4Pase protease inhibitor mixture. The eluates from the SA-A columns are incubated overnight (12–15 hours) with 1/200 to 1/400 volumes of immobilized wheat germ agglutinin (WGA-agarose or WGA-A; Vector Labs, Burlingame, Calif.). The WGA-A is pelleted by centrifugation, washed twice with 50–100 volumes of solubilization buffer+0.15% D:L (after removing the supernatants containing material not bound to WGA) and then either: (A) eluted with 8 mM triacetylchitotriose (TAC; Sigma) in solubilization buffer+ 0.15% D:L (3 sequential elutions where resin is mixed with 2 volumes of elution buffer at room temperature for 15–20 minutes, pelleted by centrifugation and supernatant removed and saved) or B. solubilized directly by addition of 1×Laemmli sample buffer and heating at 90° C. for 10–15 minutes. These samples are analyzed by SDS-PAGE and silver staining. The nonbound supernatants from the WGA-binding step are concentrated, solubilized in 1×Laemmli sample buffer and analyzed by SDS-PAGE and silver staining.

7. Cloning Candiate Rat Brain Opioid Receptor cDNAs

Candidate partial-length rat brain opioid receptor cDNAs are obtained using several mRNA and cDNA sources and several oligonucleotide primers for PCR amplification. pPCR4A is a 700 basepair (bp) pPCRII (In Vitrogen) subclone of a partial cDNA amplified from single strand cDNA prepared from whole rat brain using 35 cycles at 94° C. for 1 minute, 55° C. for 1 minute and 72° C. for 1 min and 20-base oligonucleotide (5' AGA CCG CCA CCA ACA TAT AC3'SEQ ID NO:3) and (5' GCT TGA AGT TCT CGT CCA GG3'SEQ ID NO:4) that are complementary to mouse μ-opioid receptor sequences. Sequence analysis, following manual sequencing, reveals an open reading frame predicting amino acids similar to those of the murine μ-opioid receptor, and identical to 23 amino acids sequenced from opiate receptor protein preparations.

The 700 bp insert from pPCR-4A is excised with EcoRI, radiolabelled by random priming to specific activities of $10^9$ dpm/μg, and used to screen 5×10⁶ plaques from a oligo dT-primed rat cerebral cortex lambda ZAP cDNA library that was selected so that inserts are >1.5 kb in size (p6=26). Hybridization is performed at 30° C. in buffer contained 29% formamide and 6×SSC, washing is at 50° C. in 0.4× SSC/0.1% SDS, and 2 days' autoradiographic exposure is used. Plasmids are autoexcised from λ-Zap phage DNA grown from positive plaques as described (p6=26) and analyzed by restriction analyses and DNA sequencing. One clone, termed RC8-1, is subjected to complete sequencing of both strands using automated and manual methods, and subcloned into pcDNA1(InVitrogen) to yield pcDNA1RC8-1. DNA sequences are analyzed using conventional methods.

8. Characterizing RC8-1 as a μ-opiate receptor (μOR) cDNA

COS cells are transfected by electroporation with 20 ug/10⁷ cells pcDNA1RC8-1-1 or pcDNA1 vector. Transfected COS cells are plated in DMEM containing 10% FBS, cultured for 2–3 days, and tested for opiate receptor expression by radioligand binding.

For typical radioligand binding assays, medium is removed from 150 mm plates containing 5×10⁶ COS cells, plates are rinsed briefly with 50 mM Tris buffer (pH 7.4), and cells are harvested by scraping. Membranes are prepared at 4° C. by polytron homogenization in Tris buffer, discarding material pelleted by 15 min 1000×g centrifugation, and retaining membrance fractions pelleted by a second centrifugation for 30 min at 46,000×g. Membrane fraction protein concentrations are determined by the Bradford method (Biorad). Membranes from 10⁶ COS cells, corresponding to 50 ug protein, are resuspended in 0.5 ml Tris buffer with various labelled and unlabelled compounds and incubated for 90 min at 22° C. Binding is terminated by filtration through GFB filters (Whatman) and 3 washes with 4 ml Tris buffer at 4° C. using a Brandel filtration device. In some assays, NaCl, $MgSO_4$, GTP to ATP are added to incubations (P8-10=29-31). Radioligands include [H]DAMGO [D-Ala2,N-methyl-Phc4,Glyo15] enkephalin; 60 Ci/mmole, Amersham), [H]DPDPEpCl [D-Pen2,4'-Cl-Phe4,D-Pen5]enkephalin; 51 Ci/mmole, NEN), [H]DALE (D-Ala2,D-Leu5 enkephalin: 37 Ci/mmole, NEN), and [H]U-69,593 (57 Ci/mmole Amersham). Radioactivity is assesed in a Beckman liquid scintillation counter at 40 efficiency.

9. μOR Expression

RNA is prepared from rat tissues that are rapidly dissected and frozen at −70° C. 20 μg of total RNA is prepared and electrophoresed along with molecular weight standards (BRL) and transferred to nylon membranes. Blots are hybridized with the 2.2 kb [³²P]-random-primed insert of pcDNA1RC8-1 in 5×SSPE/1% SDS/150% formamide/2.5× Denhardt/200 μg/ml herring sperm DNA at 42° C. overnight, washed twice in 0.4×SSC/0.5% SDS for 30 min at 52° C., and radioactive patterns identified using a phosphoimaging molecular dynamics device following overnight exposures.

RNase protection assays use incubation of 5 μg of RNA and a [³²P]-labeled cRNA transcribed from the T7 promoter of pPCR4A linearized with BamH1 to form a 400 basepair fragment, under conditions described by the manufacturer (V1=40), with detection of protected fragments using a phosphoimaging system.

Figure 1B:
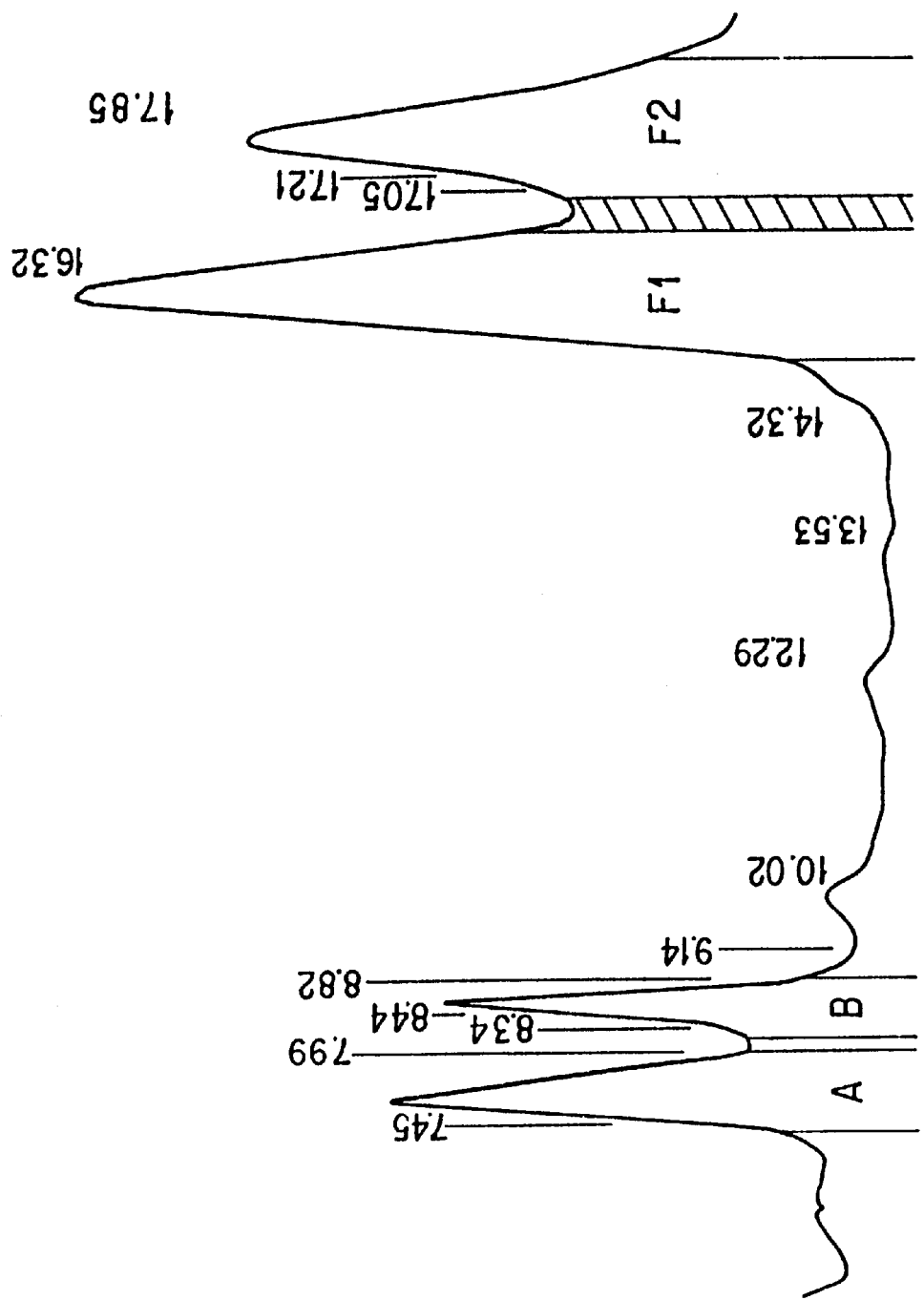
Figure 2A:
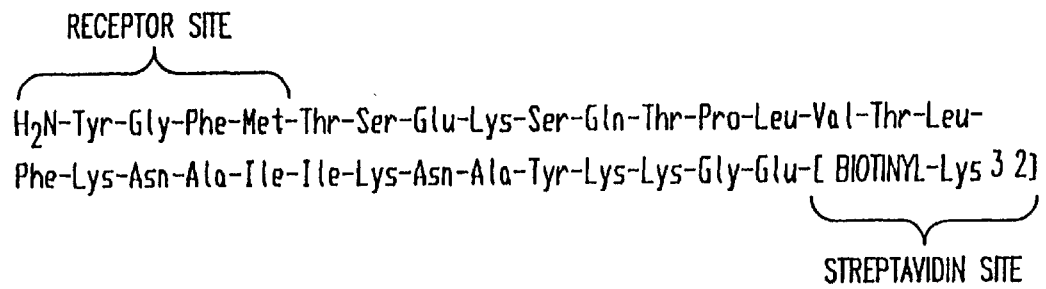
FIG. 2. Relative Receptor Binding Activities of Biotinylated β-endorphin (SEQ ID NO:13) and Nonbiotinylated β-endorphin. Rat brain membranes (30 μg per well) are incubated with [$^{125}$I]-endorphin (100,000 cpm per well) in the microtiter plate assay as described in Experimental Procedures. 2.A. Binding incubations are for 1 hour.
Figure 2B:
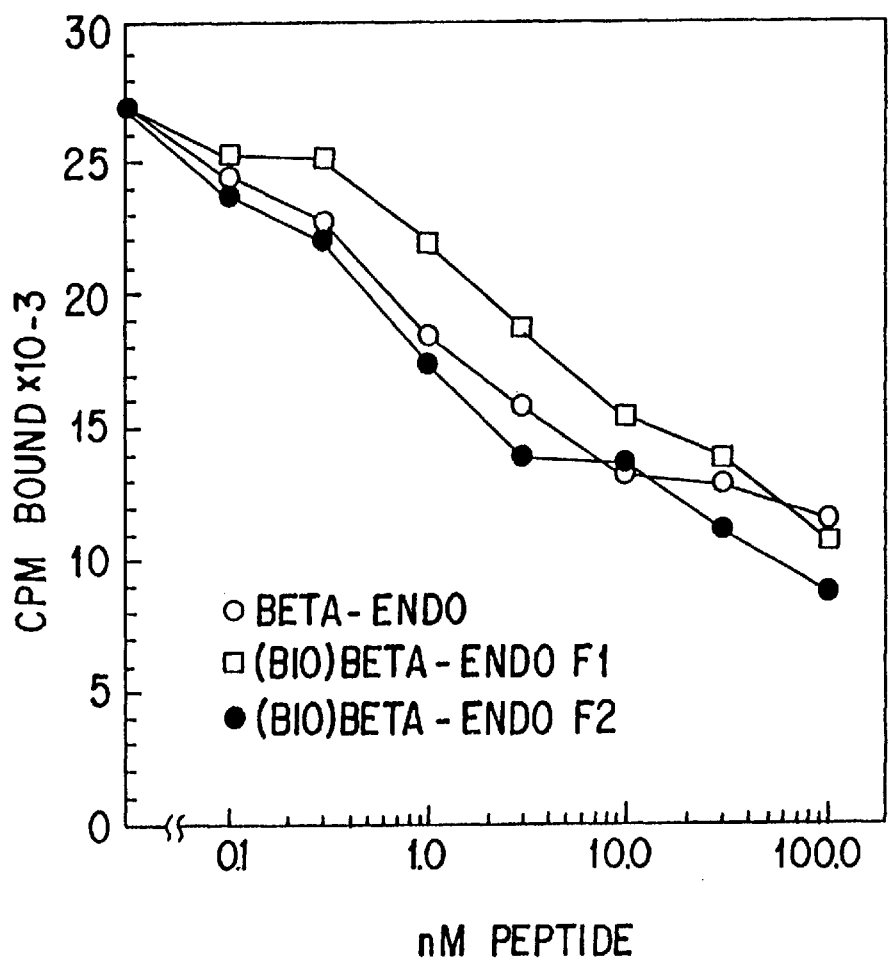

For in situ hybridization, 10 μm cryostat sections through the diencephalons of rats perfused with PLPG (0.5% paraformaldehyde, 1% glutaraldehyde, 75 mM lyside HCl, 37.5 mM $Na_2HPO$ pH 7.4 and 10 mM sodium periodate) (W=41) are thaw mounted onto slides pretreated with Denhardt's solution, 0.02% Ficoll, 0.02% polyvinylpyrrolidone, 0.02% bovine serum albumin, poly-D-lysine coating and acetylation, and are hybridized with 40- and 50-base ³⁵S-labelled oligonucleotide hybridization probes that are complementary to bases encoding amino acids indicated in FIG. 1 and labelled by a primer extension method to ca.2×10 Ci/mMole and gel-purified as described (W=41). Hybridization at 37° C. overnight in a complexbuffer is followed by washing at 50° C. and emulsion autoradiography with 2 week exposures, emulsion development, tissue section staining, and analyses. Grain densities overlying individual neurons are counted and analyzed, with positively-hydridizing neurons identified as those with densities more than five times background autoradiographs values. Neurons are identified based on size, shape, nuclear profiles, and frequent presence of nucleoli.

10. Characterization of Soluble Complexes Between [¹²⁵I]β-Endorphin and Opioid Receptor An initial attempt is made to determine whether opioid receptors can be manipulated in the same general ways as somatostatin receptors (U.S. Ser. No. 07/677,003 now U.S. Pat. No. 5,225,543, issued Jul. 6, 1993 and U.S. Ser. No. 07/677,009). The first experiment is conducted to observe whether radioligand binding to membranes followed by detergent solubilization produce R:L complexes that are stable enough for purification and yet readily dissociable under relatively mild conditions (i.e., GTP, salt, pH changes, etc.). To determine this, [¹²⁵I]β-endorphin is bound to rat brain membranes and solubilized membranes are assayed for the presence of intact complexes between [¹²⁵I]β-endorphin and receptor (R:L complex).

The assay for R:L complex exploits the well known glycoprotein nature of receptors which, like most cell surface proteins, contain covalently linked carbohydrate. The ligand, β-endorphin, is not glycosylated and will not bind to a carbohydrate-binding lectin, such as wheat germ agglutinin (WGA). Binding of the radioligand, solubilized after the binding step, to immobilized WGA is considered to reflect binding of the R:L complex to WGA via oligosaccharide groups on the receptor.

Because opioid receptors appear to be coupled to G proteins, dissociation of the R:L complex by a GTP analog is tested. This is done by incubating the solubilized preparations with GTP-γ-S prior to incubation with WGA-agarose. The effects of high salt concentrations and, separately, of low salt concentrations in combination with GTP-γ-S on R:L complex dissociation are also tested. The results are shown in Tables 1 and 2 below:

Table 1. Binding of Solubilized [¹²⁵I]β-Endorphin: Opioid Receptor Complex to WGA-Agarose and Dissociation of the Complex by GTP-g-S and NaCl. I. Rat brain membranes are incubated with [¹²⁵I]β-endorphin as previously described. The "total" binding sample is incubated with only [¹²⁵I]β-endorphin. The "nonspecific" binding sample is incubated with [¹²⁵I]β-endorphin plus 10⁻⁶ M nonlabelled β-endorphin. After the binding step, the membranes are solubilized as described previously. CPM of [¹²⁵I]β-endorphin in the 100,000×g supernatant are counted as described previously. Some samples are held on ice as an internal standard for the ratio of total to nonspecific cpm in the starting material ("A. 100,000×g supernatant"; see "A/B" ratio). Other samples ("B. Supernatants+WGA-agarose") are warmed to room temperature and then receive 100 μM GTP-g-S (Sigma; diluted from a 2 mM stock solution in $H_2O$), 500 mM NaCl (diluted from a 5 M stock solution in $H_2O$) or no treatment and are further incubated for 10 minutes at room temperature. Then all samples are placed on ice, mixed with 60 μl of immobilized wheat germ agglutinin (WGA-agarose; Vector Labs, Burlingame, Calif.) and incubated for 2 hours at 4–8° on a tube rotator. Then the WGA-agarose is pelleted by centrifugation, the supernatants are removed and the WGA-agarose is washed once in solubilization buffer+0.15% D:L and counted for radioactivity.

TABLE 1

| Samples | A. Total | B. Non-Specific | A/G | % Decrease in R:L Complex |
|---|---|---|---|---|
| A. 100,000 × g Supernatant[#] | — | — | 6 | — |
| B. Supernatants + WGA-agarose... | | | | |
| Untreated | 16,602 | 249 | 67 | — |
| GTP (100 μM GTP-g-S) | 10,981 | 213 | 52 | 34% |
| 500 mM NaCl | 2,092 | 172 | 12 | 88% |

Notes:
This sample is not incubated with WGA-agarose. Total cpm per 280 ul is 37,461 (total) and 6,326 (nonspecific).
*Specific cpm bound to WGA-agarose from the untreated sample is considered to be in intact R:L complex.

Table 2. Binding of solubilized [$^{125}$I]β-endorphin: opioid receptor complex to WGA-agarose and dissociation of the complex by GTP-g-S and NaCl. II. All steps are done essentially as in Table 1 above except that here GTP-γ-S is tested either alone or in the presence of different concentrations of NaCl. Samples of 1.5 ml volume are mixed with 0.35 ml of WGA-agarose.

TABLE 2

| | CPM of [$^{125}$I]β-Endorphin Bound to WGA-Agarose | | | |
|---|---|---|---|---|
| Sample | A. Total | B. Non-Specific | A/B | % Decrease in R:L Complex |
| Untreated GTP (100 μM) | 115,219 | 1,823 | 63 | — |
| GTP-g-S | 88,479 | 1,823 | 48 | 24% |
| GTP + 25 mM NaCl | 28,292 | 1,609 | 17 | 77% |
| GTP + 50 mM NaCl | 13,340 | 1,517 | 9 | 90% |
| GTP + 100 mM NaCl | 8,872 | 1,248 | 7 | 93% |

Several conclusions are reached from reviewing the results in Tables 1 and 2. First, the membrane bound complex between [$^{125}$I]β-endorphin and its receptor is solubilized mostly in intact form. This is shown by the adsorption of a high proportion of the solubilized [$^{125}$I]β-endorphin to immobilized WGA. Not only is a high proportion of the specifically bound radioligand adsorbed to WGA, as would be expected if it is bound to the receptor, but WGA selects for specifically bound material. This is shown by the large increase in the ratio of total cpm/nonspecific cpm in the WGA-bound material. Also, the soluble R:L complex is stable enough to be separated from free ligand in a step taking 2–3 hours. This predicts that a biotinylated β-endorphin is used to form a R:L complex that could be adsorbed in intact form to immobilized streptavidin. Further, binding to immobilized WGA serves as an assay for the soluble R:L complex, and binding to WGA serves as a purification step for the receptor. Finally, the R:L complex is easily dissociated. This provides a means for eluting the receptor from an affinity column. For example, a soluble complex between the receptor and biotinyl β-endorphin could be bound to immobilized streptavidin and the receptor then eluted by GTP (partial elution), GTP+NaCl or NaCl.

The interactions of GTP with low concentrations of salt to cause dissociation of receptor and ligand is consistent with the known properties of opiate receptors. Later results in receptor purification experiments show that lower salt concentrations do not affect stability of this R:L complex and thus the GTP/salt interactions are synergistic.

Characterization of Biotinylated β-Endorphin

The two fractions of biotinylated β-endorphin are assayed for binding to rat brain opioid receptor by competition with [$^{125}$I]β-endorphin. The $IC_{50}$s for reduction of radioligand binding by competition with cold ligand are: β-endorphin, 1 nM; biotinyl-β-endorphin (F1), 1 nM; and biotinyl-β-endorphin (F2), 5 nM. Thus, both fractions of biotinylated β-endorphin show high affinity binding to opioid receptor. The F1 fraction consists of two peptides with molecular masses, identified by mass spectroscopy, of 3816 and 3875 daltons. The F1 fraction contains only the 3816 dalton species, the expected mass for biotinyl-β-endorphin. What is shown here is that heating the F1 fraction for 5 min. at 50° C. eliminates the 3875 dalton species. Thus there is only one species of biotinyl-β-endorphin, with a mass of 3816 daltons, by mass spectrometry. Before further use, the F1 fraction is heated at 50° C. for 5 min. This material has been reanalyzed for binding to receptors in rat brain membranes by competition vs. [$^{125}$I]β-endorphin and it binds with a protency very similar to that of β-endorphin. The $IC^{508}$ are 1.2 nM for β-endorphin and 1.8 nM for biotinyl-β-endorphin.

Utility of Biotinylated β-Endorphin in Receptor Purification

Samples of brain membranes are incubated either with or without the F1 and F2 fractions of biotinyl-β-endorphin and carried through the procedure of solubilization, adsorption with immobilized streptavidin, elution and protein analysis by SDS-PAGE.

The WGA bound glycoprotein (WGA+) fractions of the eluates primarily contain a protein with MW about 66,000. Small amounts of this protein are seen in the material eluted by GTP-γ-S and much larger amounts elute with the subsequent elution with 500 mM NaCl. The appearance of this band is ligand-dependent because it does not appear in eluates from the samples done without prior binding of biotinyl-β-endorphin. The nonglycosylated (WGA−) fractions show that GTP-γ-S alone elutes nonglycosylated bands in the 30–40,000 MK (30–40K) range. These also occur only in samples incubated with biotinyl-β-endorphin and are thus ligand-dependent. Subsequent elution with 500 mM NaCl yields little if any further 30–40K MW material. Because both the F1 and F2 fractions give purification of the 66K band, they are used together in a 1:1 ratio in further experiments.

The elution of the 66K glycoprotein correlates with the effects of GTP-γ-S on stability of the soluble R:L complex. Thus 100 μM GTP-γ-S gives only partial dissociation of the soluble R:L complex and partial elution of the 66K glycoprotein. This band is considered to be the opioid receptor and will be referred to as such. It will also be referred to as "66K glycoprotein".

In a similar experiment, the 30–40K, GTP-γ-S eluted protein specifically purified by biotinyl-β-endorphin is reactive with anti-G protein antiserum (FIG. 4). In this experiment, biotinyl-NH-[Leu$^8$, D-Trp $^{22}$, Tyr$^{25}$]SRIF-28 (bio-S28); and biotinyl-β-endorhin are used to purify SRIF and opioid receptors, respectively by similar techniques. Both purifications employ essentially the same steps: binding of biotinylated ligand to intact membranes (from GH$_4$C$_1$ pituitary tumor cells and brain); solubilization of intact R:(bio)L complex; binding of R:(bio)L complex to streptavidin-immunoreactive material in the 40K size range only with the samples where receptor is complexed with biotinyl-ligand. Samples where the receptor is unoccupied or occupied by non-biotinyl ligand show no evidence of G$_{i\alpha}$.

Figure 5A:
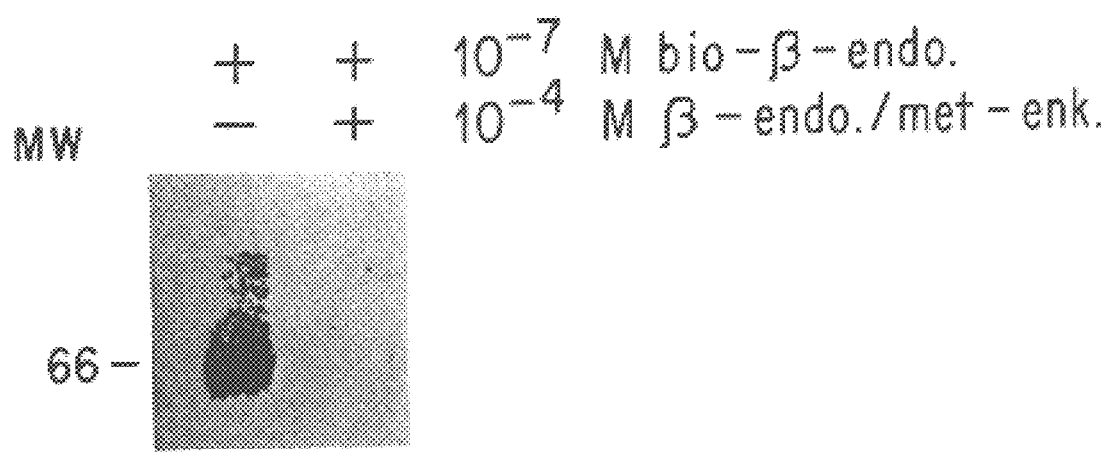
FIGS. 5A–5B. Effects of Competition by Non-Biotinylated Opioid Ligands on Purification of Receptor Bands by Bio-β-Endorphin. Competition with biotinyl-β-endorphoin in the binding step is by 50 μM β-endorphin+50 μM met-enkephalin (A) or by 40 μM naloxone (B). In B, 20 μM naloxone is also added to the 100,000×g supernatant before incubation with streptavidin-agarose because of the relatively high rate of dissociation of naloxone from opioid receptors. Elution from SA-A is with 500 mM NaCl. Eluates are processed by adsorption to WGA, eluted from WGA by TAC and analyzed by SDS-PAGE as described in Experimental Procedures 6.
Figure 5B:
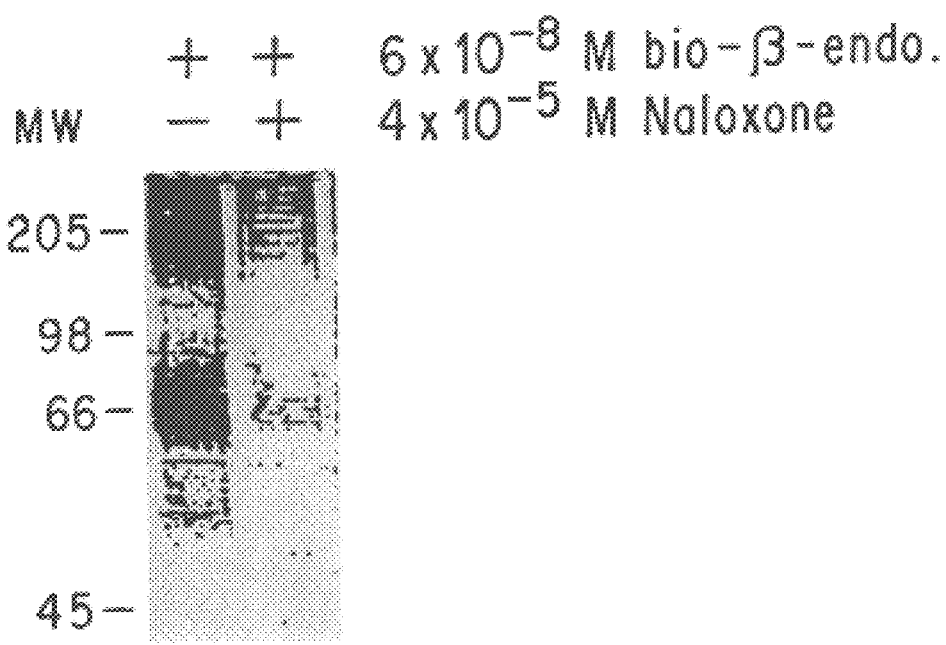
Figure 6:
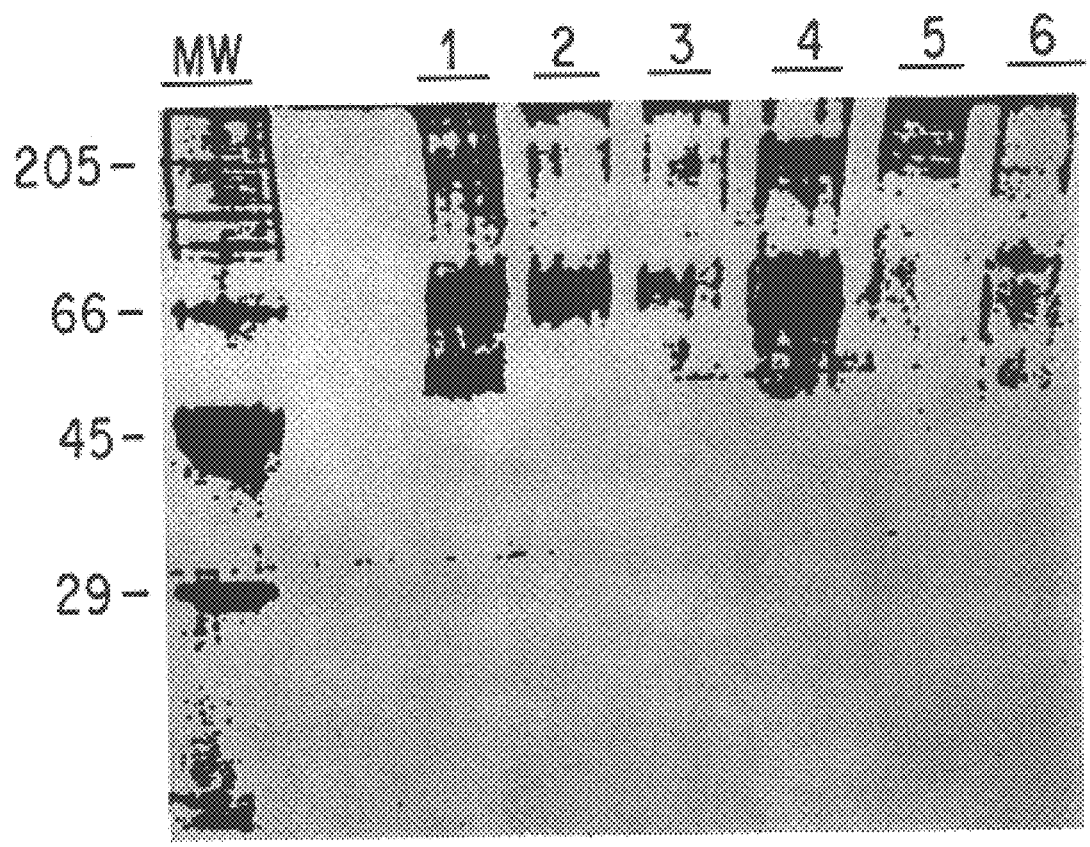
FIG. 6. GTP-Na$^+$ Interactions in Elution of Opioid Receptor from Streptavidin-Agarose. I. Receptor purification is carried out as described in Experimental Procedures. 6. up to the point of washing the SA-A columns. Two SA-A columns are then eluted in different ways as described in the text. The eluates are processed by adsorption to WGA, elution from WGA with TAC and analysis of the TAC eluates by SDS-PAGE.
Figure 7:
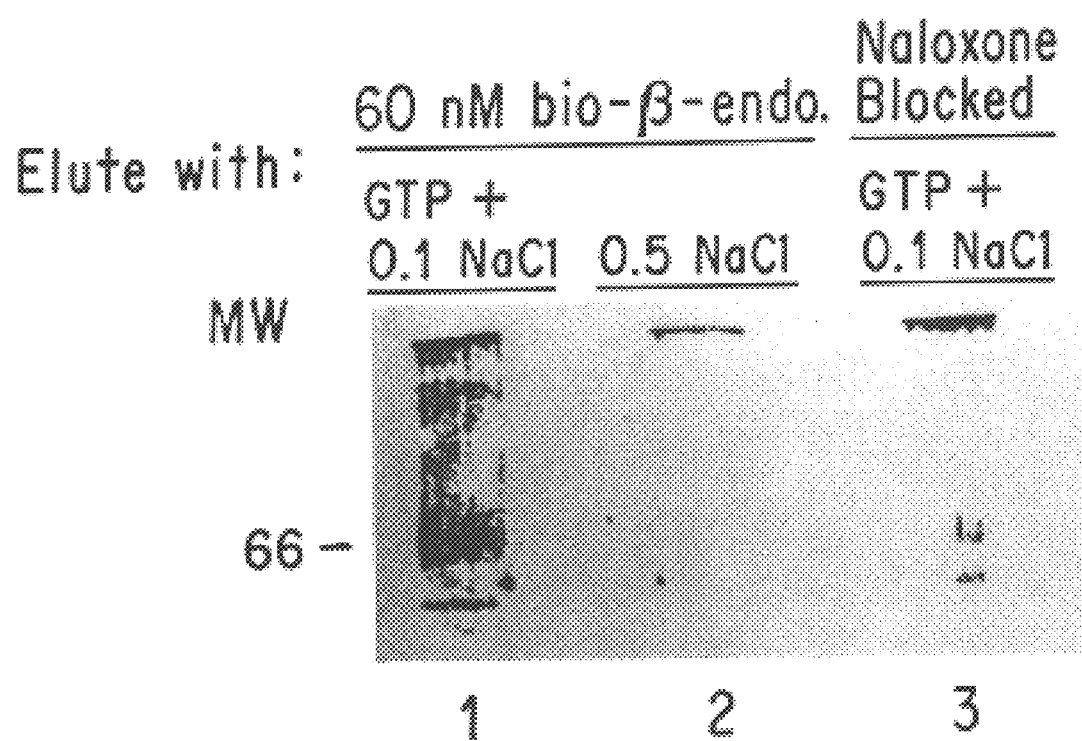
FIG. 7. GTP-Na$^+$ Interactions in Elution of Opioid Receptor from Streptavidin-Agarose. II. Receptor purification is carried out as described for FIG. 6 up to the point of washing the SA-A columns. Elution is by 100 μM GTP-100 mM NaCl (1) and then by 500 mM NaCl (2). Further processing of the eluates is as described for FIG. 6.
Figure 8:
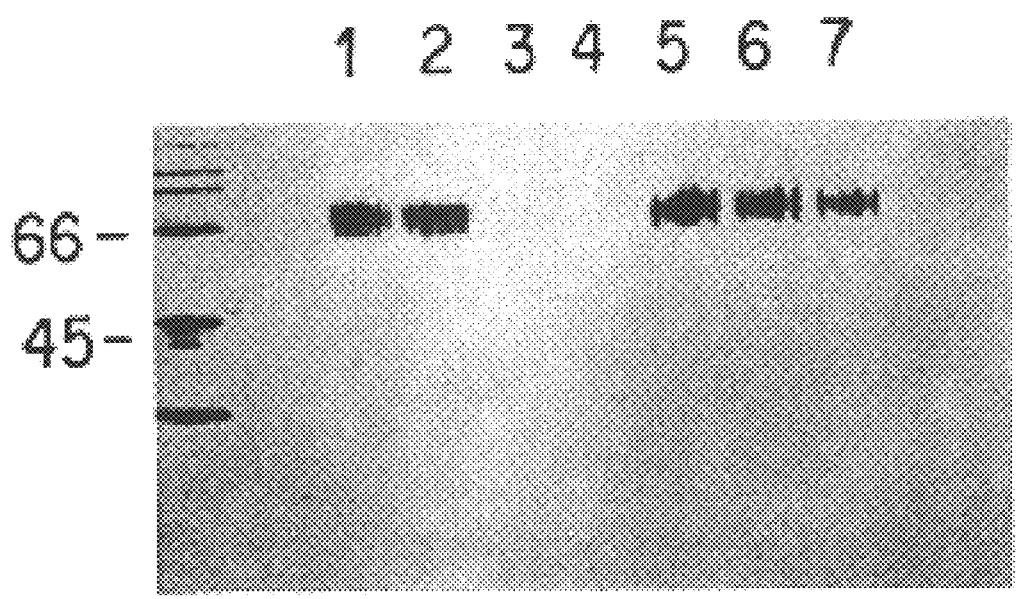
FIG. 8. Competitive Binding of Mu and Delta Receptor-Specific Peptide with β-Endorphin for Binding with Opioid Receptor. This 11% SDS-PAGE gel illustrates the mu-subtype identity of the isolated receptor protein. Lanes 3 and 4 demonstrate the ability of a peptide having preferential binding with a mu-subtype receptor to competitively inhibit binding of a biotinylated β-endorphin to the receptor, thereby preventing isolation of the 66 kDa protein from rat membranes using the biotin-avidin affinity chromatography. Lanes 5, 6 and 7 represent competitive binding using a delta-subtype specific peptide which permits recovery of the 66 kDa protein.
Figure 12A:
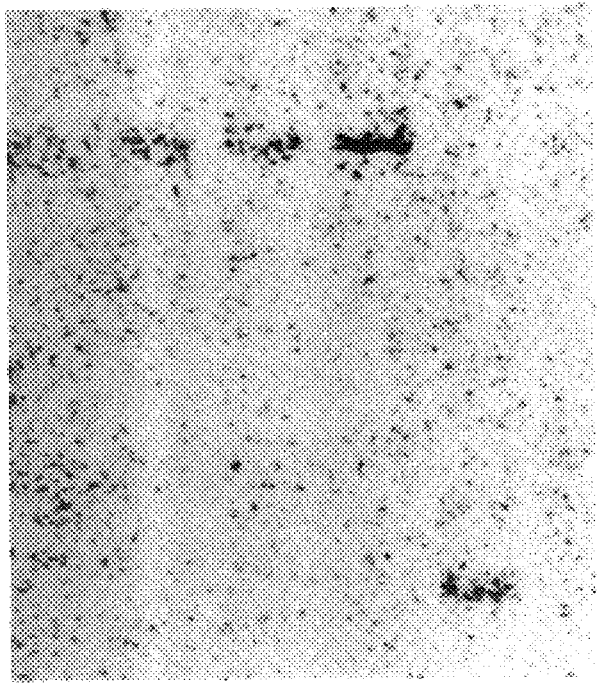
FIGS. 12A–12D. Expression of μ-opiate receptor RC8-1 mRNA. A. Northern analyses and phosphoimager autoradiogram of μ-opiate receptor mRNA hybridization to radiolabeled kRC8-1 cDNA in 20 μg total RNA extracted from rat thalamus (lanes 1 and 2), or hypothaiamus (lane 4). Size markers (lane 3) suggest a 10.5 kb mRNA size.
Figure 12B:
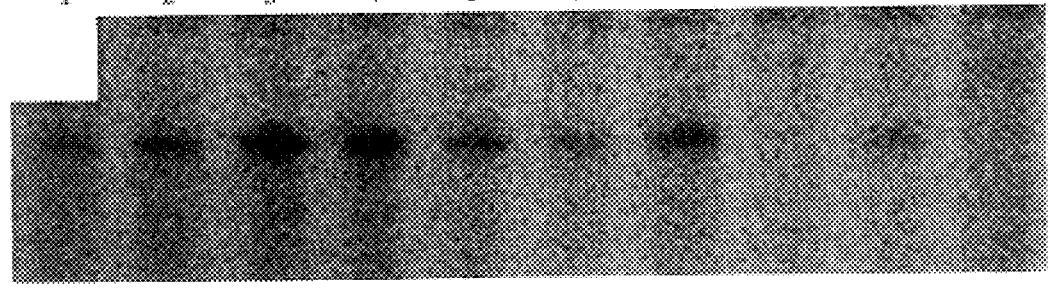
Figures 12C, 12D:
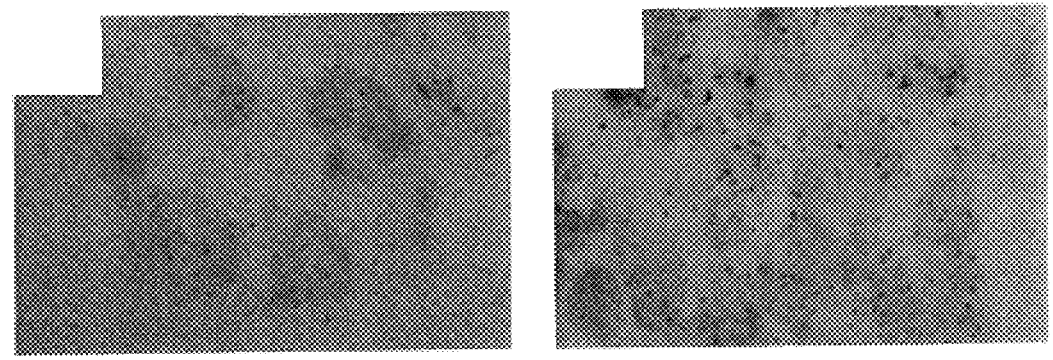

The ligand specificity of the 66K glycoprotein is further tested by blocking binding of the biotinylated β-endorphin with a large molar excess of nonbiotinylated ligand. When 100 nM biotinyl-β-endorphin (1:1 F1+F2) is competed with a combination of 50 μM β-endorphin+50 μM met-enkephalin, the yield of the 66K glycoprotein is greatly diminished. In another test of specificity, 40 μM naloxone effectively competes with 60 nM biotinyl-β-endorphin to nearly eliminate the recovery of 66K glycoprotein (FIG. 5B). In this experiment, two additional bands are seen with MWs of about 140–160,000 and 50–55,000. Since both show ligand specificity they may be receptor subtypes, proteolytically degraded receptor or receptor aggregate. While the 66K band is always the primary protein recovered by these methods, the relative amounts of the 140–160K and 50–55K bands are variable.

The SA-A column is first washed with 1 mM EDTA+1 mM EGTA and then with 100 mM NaCl prior to elution with 500 mM NaCl. Since these wash steps carried out with very little loss of the 66K receptor band, they are incorporated into further procedures.

In the purifications shown above, elution of receptor from the SA-A columns is with 500 mM NaCl. This is used as an alternative to GTP because it elutes the 66K glycoprotein more effectively. However, the ability of the GTP-γ-S+lower salt concentrations (25–100 mM NaCl) to dissociate the R:L complex suggests that it is possible to elute the receptor by avoiding high salt concentrations. This is tested by adsorbing the solubilized complex between receptor and biotinyl-β-endorphin to SA-A, dividing the sample into two different columns and eluting in two different ways as follows: A. elute sequentially with 100 pM GTP/75 mM NaCl and with 500 mM NaCl; B. wash with 100 mM NaCl and then elute with 500 mM Nacl. From the first SA-A column, elution with 100 μM GTP/75 mM NaCl yields nearly all of the 140–160K and 50–55K bands and a large proportion of the 66K band. The remainder of 66K material is eluted with 500 mM NaCl. From the second SA-A column, very little material is eluted by 100 mM NaCl while 500 mM NaCl elutes all of the ligand specific bands. Specificity is shown in this experiment by a naloxone block, where naloxone competes with biotinyl-β-endorphin for receptor binding and the 140–160K, 66K and 50–55K bands are not seen.

The results are significant for two reasons. First, they provide further correlations between the recovery of 66K protein and known properties of opioid receptors. A NA$^+$/GTP interaction is shown at two levels; by dissociation of the soluble R:L complex (Tables 1 and 2) and by recovery of specific receptor bands upon elution of affinity columns. Because the NA$^+$/GTP interaction is such a well documented property of opioid receptor binding, this data increases the probability that the 66K glycoprotein and other specific bands are, in fact, opioid receptor proteins. It is further shown that elution with 100 μM GTP/100 mM NaCl gives complete elution of the 66K band and other ligand specific species from the SA-A column. Thus subsequent elution with 500 mM NaCl yields little further ligand specific protein. However for routine receptor purification, elution with 500 mm Nacl alone provides a good yield of receptor which can be further purified on wheat germ agglutinin to yield sequencing quality receptor.

Pharmacology of Isolated Receptor

Further pharmaceutical analysis is done to determine the subtype of the 66 kDa receptor protein. Two different peptides, one known to exhibit mureceptor selective binding ([D-Ala$^2$, N-MePhe$^4$, glyol$^5$]enkephalin or DAGO; Bachem; 300 fold selectivity for mu over delta) and the other known to exhibit delta receptor selective binding ([D-Pen$^{2,5}$, pCL-Phe$^4$]enkephalin or pCl-DPDPE; 500-fold selectivity for delta over mu) are used to block binding of biotinyl-β-endorphin to rat brain membranes. This pair of ligands is appropriate because their affinities for their respective receptors are very similar (approximately 1 mM K$_D$). Each incubation contains 3 nM biotinyl-62 -endorphin, and the blocking peptides are included at 50, 500, and 5000 nM. The ligand mixtures are incubated with unsolubilized membranes for one hour at room temperature and then purification of the receptor proceeds as described herein. A summary of the condition is provided in Table 3.

The ability of the respective peptides to block β-endorphin binding is determined by observing the relative recovery of biotinylated β-endorphin bound 66 kDa protein from each sample. It can be seen that the 66 kDa protein is recovered in about the same amounts from the control as when the pCl-DPDPE is used as a competitor. In contrast, DAGO blocked recovery of receptor almost completely at 500 nM and completely at 5000 nM, thereby confirming the identity of the protein as a mu-subtype opioid receptor.

TABLE 3

| Sample | 3 nM Biotinyl-b-Endorphin | DAGO* | pCL-DPDPE# |
|---|---|---|---|
| 1 | + | — | — |
| 2 | + | 50 nM | — |
| 3 | + | 500 nM | — |
| 4 | + | 5000 nM | — |
| 5 | + | — | 50 nM |
| 6 | + | — | 500 nM |
| 7 | + | — | 5000 nM |

Notes:
*mu-specific
delta-specific

Identification of 700 base pair C-DNA Clone pPCR4A

Analyses of products derived from PCR amplification of rat brain cDNA using oligonucleotides complementary to regions of the mouse μ-opioid receptor identify the 700 base pair cDNA clone pPCR4A. This cDNA display 70% nucleotide sequence identity to the rat μ-opioid receptor cDNA and homology with cDNA sequences of other G-linked receptor. One open reading frame of the pPCR4A sequence matches each of the 23 amino acids sequenced from a μ-opioid receptor protein preparation.

Several rat cerebral cortical cDNAs hybridize with radio-labeled pPCR4A hybridization probes; one 2.2 kb cDNA termed RC8-1 is selected for further analysis. Sequence analyses reveals that 996 RC8-1 SEQ ID NO:1 nucleotides encode an open reading frame of 332 amino acids with 63% amino acid identity to sequences of the μ-opiate receptor, good homology to other neuropeptide receptors, and more distant homology to an "opiate binding protein" receptor, a catecholamine receptor and rhodopsin. Hydrophobicity analyses reveals at least seven hydrophobic putative membrane spanning domains of 20–24 amino acids whose sequences are especially conserved with other G-linked receptors. Threonine residue 23 is found in a context especially favorable for protein kinase A phosphorylation. One consensus sequence for N-linked glycosylation at amino acid 11 is observed in the N-terminal domain (Z=44).

Figure 3:
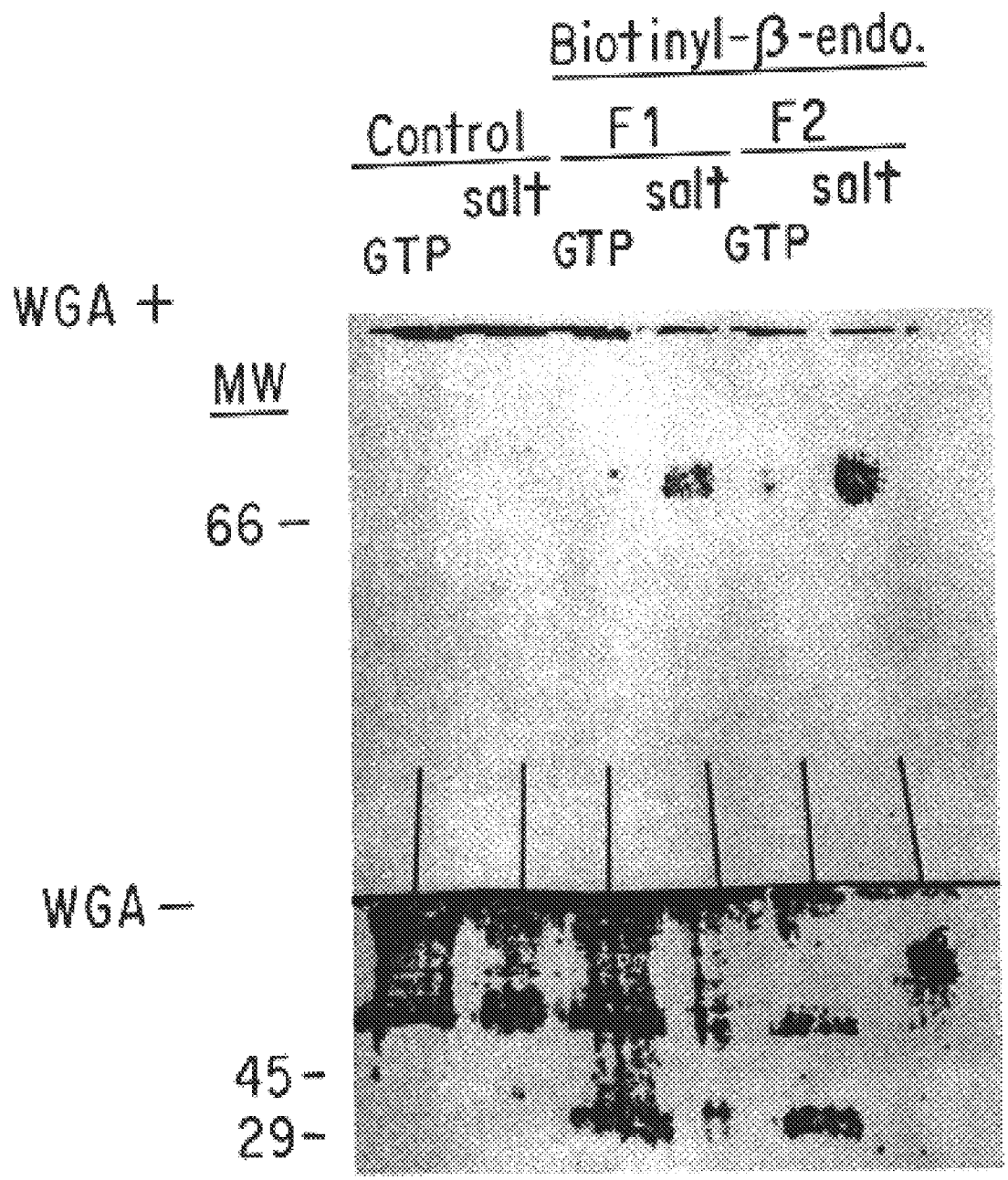
FIG. 3. Efficacy of Biotinyl-β-Endorphin in Receptor Purification. Rat brain membranes (each containing 30 mg of protein) are incubated with: (a) No ligand, (b) 100 nM biotinyl-β-endorphin F1 or (c) 100 nm biotinyl-p-endorphin F2 and solubilized in 0.15% D:L (all procedures as in Experimental Methods. 1.–3.: One exception in this particular experiment is that the binding and wash step is done in 50 mM potassium phosphate [pH 7.4]+0.1% BSA). The 100,000×g supernatants are then incubated with immobilized streptavidin (streptavidin agarose or SA-A) and the SA-A is poured into chromatography columns and washed with solubilization buffer+D:L as described in Experimental Procedures. 6.). Each column is eluted at room temperature, first with 4 column volumes of 100 μM GTP-γ-S and then with 4 column volumes of 500 mM NaCl (both eluants in solubilization buffer_0.15% D:L+1/1000 volume of 100× 4Pase. The eluates are then incubated with WGA-agarose and processed for analysis by SDS-PAGE of glycoproteins (proteins bound to WGA-A) and nonglycoproteins (proteins not bound to WGA-A) as described in Experimental Procedures. 6. and 7.

COS cell expression of RC8-1 in the expression vector pcDNA1 yield naloxone-blockable, high affinity specific binding of [$^H$] DAMGO and [$^3$H] DADLE binding saturation experiments are most consistent with a single population of binding sites for each ligand, with KK values of 0.4 and 0.5 nM, respectively. [$^2$H] DAMGO binding is reduced by addition of Na$^+$ or GTP to incubations, but not by adding ATP (FIG. 3). Mg$^{++}$ addition increases binding by COS cell expression of RC8-1 in the expression vector pcDNA1 yielded naloxone-blockable, high effinity specific binding of [$^3$H]DAMGO and [$^3$H]DADLE, with no appreciable specific recognition of [$^3$H]DPDPE or [$^3$H]U 69,593, that is not present in cells transfected with vector alone. Scatchard analysis of [$^3$H]DAMGO and [$^3$H]DADLE binding saturation experiments are most consistent with a single population of high affinity binding sites for each ligand, with Kn values on 0.4 and 0.5 nM respectively. [$^3$H]DAMGO binding is reduced by addition of Na+ of GTP to incubations. [$^3$H]DAMGO binding is displaced by a number of opioid compounds in stereoselective fashion. Pharamcologically active (−)naloxone and dextrorphan isomers display substantially greater potency than pharmacologically less active (+)naloxone and dextrorphan isomers. Morphine, DADLE, (−)naloxone, naloxonazine, ethylketocyclazocino and bromazocino displace binding of [$^3$H]DAMGO with high potency (Table 1). DPDPE and p-Cl-DEDPE, relatively mu-selective, U 50,488 and U 69,593, relatively k selective, display substantially less potency. These potencies display a good correlation with values described for affinities for the mu-opioid receptor, but poor correlations with affinities documented at mu or k-opioid receptors. Goldstein, A. & Naidu, A. (1989) Mol. Pharmacol. 36, 265–272. [$^3$H] DAMGO binding could be displaces by a number of opioid compounds in stereoselective fashion. Pharmacologically-active (−) naloxone and levorphan isomers display substantially greater potency than their pharmacologically-inactive isomers. Morphine displaces binding with high affinity shared by DADLe, (−) naloxone, naloxonazine, and bremazocine (FIG. 4A). DPDPE, relatively $\mu$-selective, and U-50, 488, relatively $\mu$-selective, displayed substantially loss potencies. These protencies display a good correlation with values described for affinities for the $\mu$-opioid receptor, but poor correlations with affinities documented at $\mu$-opioid receptor.

Initial Northern analyses of the distribution of mRNA hybridizing with-radiolabeled RC8-1 hybridization probes suggests that relatively high expression levels of an 10.5 kb mRNA are found in the thalamus. RNase-protection assays of greater sensitivity are able to detect protected fragments consistent with significant $\mu$OR mRNA presence in the thalamus, cerebral cortex, straitum, hypothalamus, midbrain, hippocampus, brainstern, and spinal cord but not cerebellum or liver. In situ hybridization studies identify grain densities more than five-fold greater than autoradiographic background over cells in several thalamic nuclei that displayed the size, shape, and presence of nucleoli characteristic of neurons.

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 2135 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Rattus rattus (vii) IMMEDIATE SOURCE:
        (B) CLONE: mu receptor cDNA (xi) SEQUENCE DESCRIPTION: SEQ ID NO:1:

```
CTACCTAGTC CGCAGCAGGC CTTCAGCACC ATGGACAGCA GCACCGGCCC AGGGAACACC      60

AGCGACTGCT CAGACCCCTT AGCTCAGGCA AGTTGCTCCC CAGCACCTGG CTCCTGGCTC     120

AACTTGTCCC ACGTTGATGG CAACCAGTCC GATCCATGCG GTCTGAACCG CACCGGGCTT     180

GGCGGGAACG ACAGCCTGTG CCCTCAGACC GGCAGCCCTT CCATGGTCAC AGCCATTACC     240

ATCATGGCCC TCTACTCTAT CGTGTGTGTA GTGGGCCTCT TCGGAAACTT CCTGGTCATG     300

TATGTGATTG TAAGATACAC CAAAATGAAG ACTGCCACCA ACATCTACAT TTTCAACCTT     360
```

-continued

```
GCTCTGGCAG ACGCCTTAGC GACCAGTACA CTGCCCTTTC AGAGTGTCAA CTACCTGATG      420

GGAACATGGC CCTTCGGAAC CATCCTCTGC AAGATCGTGA TCTCAATAGA TTACTACAAC      480

ATGTTCACCA GCATATTCAC CCTCTGCACC ATGAGCGTGG ACCGCTACAT TGCTGTCTGC      540

CACCCAGTCA AAGCCCTGGA TTTCCGTACC CCCCGAAATG CCAAAATCGT CAACGTCTGC      600

AACTGGATCC TCTCTTCTGC CATCGGTCTG CCTGTAATGT TCATGGCAAC CACAAAATAC      660

AGGCAGGGGT CCATAGATTG CACCCTCACG TTCTCCCACC CAACCTGGTA CTGGGAGAAC      720

CTGCTCAAAA TCTGTGTCTT TATCTTCGCT TTCATCATGC CGGTCCTCAT CATCACTGTG      780

TGTTACGGCC TGATGATCTT ACGACTCAAG AGCGTTCGCA TGCTATCGGG CTCCAAAGAA      840

AAGGACAGGA ATCTGCGCAG GATCACCCGG ATGGTGCTGG TGGTCGTGGC TGTATTTATC      900

GTCTGCTGGA CCCCCATCCA CATCTACGTC ATCATCAAAG CGCTGATCAC GATTCCAGAA      960

ACCACATTTC AGACCGTTTC CTGGCACTTC TGCATTGCTT TGGGTTACAC GAACAGCTGC     1020

CTGAATCCAG TTCTTTACGC CTTCCTGGAT GAAAACTTCA AGCGATGCTT CAGAGAGTTC     1080

TGCATCCCAA CCTCGTCCAC GATCGAACAG CAAAACTCCA CTCGAGTCCG TCAGAACACT     1140

AGGGAACATC CCTCCACGGC TAATACAGTG GATCGAACTA ACCACCAGCT AGAAAATCTG     1200

GAGGCAGAAA CTGCTCCATT GCCCTAACTG GGTCTCACAC CATCCAGACC CTCGCTAAGC     1260

TTAGAGGCCG CCATCTACGT GGAATCAGGT TGCTGTCAGG GTGTGTGGGA GGCTCTGGTT     1320

TCCTGAGAAA CCATCTGATC CTGCATTCAA AGTCATTCCT CTCTGGCTAC TTCACTCTGC     1380

ACATGAGAGA TGCTCAGACT GTATCAAGTA CTCAGAAAGA AGAGACTACC GGACACTCCT     1440

GAATCCAGCT CATGTACAGA ACCATCTGAA ACACCCAGTG GACCACAATG CTCTGTGGTA     1500

TGTGAATTTC GATCATCATA GAAGGTGACC CCTCTCTATG TAGAATTTTT ATTTTTCAAG     1560

CAAATACTTA TGACCTCATC AAAGAAAATA ATGTCACTTG TTAAATTCAC TGTAGTGATA     1620

CATAAAGTAA ATGCTACCTC TGACCTCTGA CCCAGTCACC TTCTGTAGAG AGTTCCAGTC     1680

CTTTTGTGAT GGAATACATC ATTTCCAACT TAAAACTTTC ACCTTGAAGT TATGGTCTAG     1740

TTAAGACATC AGGGGCACCT CCGTTTCTTG GTTTTGTATT GTTGAAAGA AGACGACATC      1800

TTCCTCCTTA GCTGTGTGTT GAAAATGAAA GGGATTGAAA GCACAGTGTC AACTGCAGAA     1860

TGGTTGATTC TCACTCTGAA AGGATTTACT TCGAGTTATA ATGTGGGGGT TAGGAGAGGG     1920

GCTGTTTTTT CCTAATTCCC ACCATGTCCT CTAAGTGTTC ACAAGGTCAA GTTCAGAAGG     1980

TCACCCAGTG AGTTCATCAT GCTATCATTC TGAGCAGGAA GCCAAGAATT TCGCTCTCTT     2040

CATTTTTTTC AGTAATTTCT CCACACTGCA CGCTCTTTTG TATTATTTTC CCTGATGCCT     2100

TATGAAACAG CATGATCAAA CAACAGATGG AATTC                                2135
```

(2) INFORMATION FOR SEQ ID NO:2:

(i) SEQUENCE CHARACTERISTICS:
        (A) LENGTH: 356 amino acids
        (B) TYPE: amino acid
        (C) STRANDEDNESS: single
        (D) TOPOLOGY: linear (ii) MOLECULE TYPE: protein (v) FRAGMENT TYPE: N-terminal (vi) ORIGINAL SOURCE:
        (A) ORGANISM: Rattus rattus (vii) IMMEDIATE SOURCE:
        (B) CLONE: mu receptor amino acid (xi) SEQUENCE DESCRIPTION: SEQ ID NO:2:

```
Met Arg Ser Glu Pro Thr Gly Leu Gly Gly Asn Asp Ser Leu Cys Pro
 1               5                  10                  15

Gln Thr Gly Ser Pro Ser Met Val Thr Gly Ile Thr Ile Met Ala Leu
                20                  25                  30

Tyr Ser Ile Val Cys Val Val Gly Leu Phe Gly Asn Phe Leu Val Met
                35                  40                  45

Tyr Val Ile Val Arg Tyr Thr Lys Met Lys Thr Ala Thr Asn Ile Tyr
 50                  55                  60

Ile Phe Asn Leu Ala Leu Ala Asp Ala Leu Ala Thr Ser Thr Leu Pro
 65                  70                  75                  80

Phe Gln Ser Val Asn Tyr Leu Met Gly Thr Trp Pro Phe Gly Thr Ile
                85                  90                  95

Leu Cys Lys Ile Val Ile Ser Ile Asp Tyr Tyr Asn Met Phe Thr Ser
                100                 105                 110

Ile Phe Thr Leu Cys Thr Met Ser Val Asp Arg Tyr Ile Ala Val Cys
                115                 120                 125

His Pro Val Lys Ala Leu Asp Phe Arg Thr Pro Arg Asn Ala Lys Ile
                130                 135                 140

Val Asn Val Cys Asn Trp Ile Leu Ser Ser Ala Ile Gly Leu Pro Val
145                 150                 155                 160

Met Phe Met Ala Thr Thr Lys Tyr Arg Gln Gly Ser Ile Asp Cys Thr
                165                 170                 175

Leu Thr Phe Ser His Pro Thr Trp Tyr Trp Glu Asn Leu Leu Lys Ile
                180                 185                 190

Cys Val Phe Ile Phe Ala Phe Ile Met Pro Val Leu Ile Ile Thr Val
                195                 200                 205

Cys Tyr Gly Leu Met Ile Leu Arg Leu Lys Ser Val Arg Met Leu Ser
                210                 215                 220

Gly Ser Lys Glu Lys Asp Arg Asn Leu Arg Arg Ile Thr Arg Met Val
225                 230                 235                 240

Leu Val Val Val Ala Val Phe Ile Val Cys Trp Thr Pro Ile His Ile
                245                 250                 255

Tyr Val Ile Ile Lys Ala Leu Ile Thr Ile Pro Glu Thr Thr Phe Gln
                260                 265                 270

Thr Val Ser Trp His Phe Cys Ile Ala Leu Gly Tyr Thr Asn Ser Cys
                275                 280                 285

Leu Asn Pro Val Leu Tyr Ala Phe Leu Asp Glu Asn Phe Lys Arg Cys
290                 295                 300

Phe Arg Glu Phe Cys Ile Pro Thr Ser Ser Thr Ile Glu Gln Gln Asn
305                 310                 315                 320

Ser Thr Arg Val Arg Gln Asn Thr Arg Glu His Pro Ser Thr Ala Asn
                325                 330                 335

Thr Val Asp Arg Thr Asn His Gln Leu Glu Asn Leu Glu Ala Glu Thr
                340                 345                 350

Ala Pro Leu Pro
                355
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
    (A) ORGANISM: Mus musculus (vii) IMMEDIATE SOURCE:
    (B) CLONE: DELTA RECEPTOR PRIMER 1

(xi) SEQUENCE DESCRIPTION: SEQ ID NO:3:

AGACCGCCAC CAACATATAC                                          20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Mus musculus (vii) IMMEDIATE SOURCE:
        (B) CLONE: DELTA RECEPTOR PRIMER 2

(xi) SEQUENCE DESCRIPTION: SEQ ID NO:4:

GCTTGAAGTT CTCGTCCAGG                                          20

(2) INFORMATION FOR SEQ ID NO:5:

(i) SEQUENCE CHARACTERISTICS:
        (A) LENGTH: 356 amino acids
        (B) TYPE: amino acid
        (C) STRANDEDNESS: single
        (D) TOPOLOGY: linear (ii) MOLECULE TYPE: protein (v) FRAGMENT TYPE: N-terminal (vi) ORIGINAL SOURCE:
        (A) ORGANISM: Rattus rattus (vii) IMMEDIATE SOURCE:
        (B) CLONE: MUOR-1

(xi) SEQUENCE DESCRIPTION: SEQ ID NO:5:

```
Met Arg Ser Glu Pro Thr Gly Leu Gly Gly Asn Asp Ser Leu Cys Pro
1               5                   10                  15

Gln Thr Gly Ser Pro Ser Met Val Thr Gly Ile Thr Ile Met Ala Leu
            20                  25                  30

Tyr Ser Ile Val Cys Val Val Gly Leu Phe Gly Asn Phe Leu Val Met
        35                  40                  45

Tyr Val Ile Val Arg Tyr Thr Lys Met Lys Thr Ala Thr Asn Ile Tyr
    50                  55                  60

Ile Phe Asn Leu Ala Leu Ala Asp Ala Leu Ala Thr Ser Thr Leu Pro
65                  70                  75                  80

Phe Gln Ser Val Asn Tyr Leu Met Gly Thr Trp Pro Phe Gly Thr Ile
            85                  90                  95

Leu Cys Lys Ile Val Ile Ser Ile Asp Tyr Tyr Asn Met Phe Thr Ser
            100                 105                 110

Ile Phe Thr Leu Cys Thr Met Ser Val Asp Arg Tyr Ile Ala Val Cys
            115                 120                 125
```

```
His Pro Val Lys Ala Leu Asp Phe Arg Thr Pro Arg Asn Ala Lys Ile
    130                 135                 140

Val Asn Val Cys Asn Trp Ile Leu Ser Ser Ala Ile Gly Leu Pro Val
145                 150                 155                 160

Met Phe Met Ala Thr Thr Lys Tyr Arg Gln Gly Ser Ile Asp Cys Thr
                165                 170                 175

Leu Thr Phe Ser His Pro Thr Trp Tyr Trp Glu Asn Leu Leu Lys Ile
                180                 185                 190

Cys Val Phe Ile Phe Ala Phe Ile Met Pro Val Leu Ile Ile Thr Val
                195                 200                 205

Cys Tyr Gly Leu Met Ile Leu Arg Leu Lys Ser Val Arg Met Leu Ser
    210                 215                 220

Gly Ser Lys Glu Lys Asp Arg Asn Leu Arg Arg Ile Thr Arg Met Val
225                 230                 235                 240

Leu Val Val Val Ala Val Phe Ile Val Cys Trp Thr Phe Thr His Ile
                245                 250                 255

Tyr Val Ile Ile Lys Ala Leu Ile Thr Ile Pro Glu Thr Thr Phe Gln
                260                 265                 270

Thr Val Ser Trp His Phe Cys Ile Ala Leu Gly Tyr Phe Asn Ser Cys
                275                 280                 285

Leu Asn Pro Val Leu Tyr Ala Phe Leu Asp Glu Asn Phe Lys Arg Cys
    290                 295                 300

Phe Arg Glu Phe Cys Ile Pro Thr Ser Ser Thr Ile Glu Gln Gln Asn
305                 310                 315                 320

Ser Thr Arg Val Arg Gln Asn Thr Arg Glu His Pro Ser Thr Ala Asn
                325                 330                 335

Thr Val Asp Arg Thr Asn His Gln Leu Glu Asn Leu Glu Ala Glu Thr
                340                 345                 350

Ala Pro Leu Pro
        355

(2) INFORMATION FOR SEQ ID NO:6:

(i) SEQUENCE CHARACTERISTICS:
        (A) LENGTH: 372 amino acids
        (B) TYPE: amino acid
        (D) TOPOLOGY: linear (ii) MOLECULE TYPE: protein (v) FRAGMENT TYPE: N-terminal (vi) ORIGINAL SOURCE:
         (A) ORGANISM: Mus musculus (vii) IMMEDIATE SOURCE:
          (B) CLONE: DOR-1

(xi) SEQUENCE DESCRIPTION: SEQ ID NO:6:

Met Glu Leu Val Pro Ser Ala Arg Ala Glu Leu Gln Ser Ser Pro Leu
1               5                   10                  15

Val Asn Leu Ser Asp Ala Phe Pro Ser Ala Phe Pro Ser Ala Gly Ala
                20                  25                  30

Asn Ala Ser Gly Ser Pro Gly Ala Arg Ser Ala Ser Ser Leu Ala Leu
            35                  40                  45

Ala Ile Ala Ile Thr Ala Leu Tyr Ser Ala Val Cys Ala Val Gly Leu
        50                  55                  60

Leu Gly Asn Val Leu Val Met Phe Gly Ile Val Arg Tyr Thr Lys Leu
65                  70                  75                  80
```

```
Lys Thr Ala Thr Asn Ile Tyr Ile Phe Asn Leu Ala Leu Ala Asp Ala
                85                  90                  95
Leu Ala Thr Ser Thr Leu Pro Phe Gln Ser Ala Lys Tyr Leu Met Glu
                100                 105                 110
Thr Trp Pro Phe Gly Glu Leu Leu Cys Lys Ala Val Leu Ser Ile Asp
                115                 120                 125
Tyr Asn Tyr Met Phe Thr Ser Ile Phe Thr Leu Thr Met Met Ser Val
                130                 135             140
Asp Arg Tyr Ile Ala Val Cys His Pro Val Lys Ala Leu Asp Phe Arg
145                 150                 155                 160
Thr Pro Ala Lys Ala Lys Leu Ile Asn Ile Cys Ile Trp Val Leu Ala
                165                 170                 175
Ser Gly Val Gly Val Pro Ile Met Val Met Ala Val Thr Gln Pro Arg
                180             185                 190
Asp Gly Ala Val Val Cys Met Leu Gln Phe Pro Ser Pro Ser Trp Tyr
                195             200                 205
Trp Asp Thr Val Thr Lys Ile Cys Val Phe Leu Phe Ala Phe Val Val
                210             215                 220
Pro Ile Leu Ile Ile Thr Val Cys Tyr Gly Leu Met Leu Leu Arg Leu
225                 230                 235                 240
Arg Ser Val Arg Leu Leu Ser Gly Ser Lys Glu Lys Asp Arg Ser Leu
                245                 250                 255
Arg Arg Ile Thr Arg Met Val Leu Val Val Gly Ala Phe Val Val
                260                 265                 270
Cys Trp Ala Pro Ile His Ile Phe Val Ile Val Trp Thr Leu Val Asp
                275             280                 285
Ile Asn Arg Arg Asp Pro Leu Val Val Ala Ala Leu His Leu Cys Ile
290                 295                 300
Ala Leu Gly Tyr Ala Asn Ser Ser Leu Asn Pro Val Leu Tyr Ala Phe
305                 310                 315                 320
Leu Asp Glu Asn Phe Lys Arg Cys Phe Arg Gln Leu Cys Arg Thr Pro
                325                 330                 335
Cys Gly Arg Gln Glu Pro Gly Ser Leu Arg Arg Pro Arg Gln Ala Thr
                340                 345                 350
Thr Arg Glu Arg Val Thr Ala Cys Thr Pro Ser Asp Gly Pro Gly Gly
                355                 360                 365
Gly Arg Ala Ala
        370

(2) INFORMATION FOR SEQ ID NO:7:

(i) SEQUENCE CHARACTERISTICS:
        (A) LENGTH: 389 amino acids
        (B) TYPE: amino acid
        (D) TOPOLOGY: linear (ii) MOLECULE TYPE: protein (v) FRAGMENT TYPE: N-terminal (vi) ORIGINAL SOURCE:
        (A) ORGANISM: Rattus rattus (vii) IMMEDIATE SOURCE:
        (B) CLONE: SOMAT (xi) SEQUENCE DESCRIPTION: SEQ ID NO:7:

Met Phe Pro Asn Ala Pro Pro Leu Pro His Ser Ser Pro Ser Ser Ser
```

-continued

```
  1                   5                   10                  15
Pro Gly Gly Cys Gly Glu Gly Val Cys Ser Arg Gly Pro Gly Ser Gly
                20                  25                  30

Ala Ala Asp Gly Met Glu Glu Pro Gly Arg Asn Ser Ser Gln Asn Gly
                35                  40                  45

Thr Leu Ser Glu Gly Gln Gly Ser Ala Ile Leu Ile Ser Phe Ile Tyr
                50                  55                  60

Ser Val Val Cys Leu Val Gly Leu Cys Gly Asn Ser Met Val Ile Tyr
 65                  70                  75                  80

Val Ile Leu Arg Tyr Ala Lys Met Lys Thr Ala Thr Asn Ile Tyr Ile
                    85                  90                  95

Leu Asn Leu Ala Ile Ala Asp Glu Leu Leu Met Leu Ser Val Pro Phe
                100                 105                 110

Leu Val Thr Ser Thr Leu Leu Arg His Trp Pro Phe Gly Ala Leu Leu
                115                 120                 125

Cys Arg Leu Val Leu Ser Val Asp Ala Val Asn Met Phe Thr Ser Ile
                130                 135                 140

Tyr Cys Leu Thr Val Leu Ser Val Asp Arg Tyr Val Ala Val Glu His
145                 150                 155                 160

Pro Ile Lys Ala Ala Arg Tyr Arg Arg Pro Thr Val Ala Lys Val Val
                165                 170                 175

Asn Leu Gly Val Trp Val Leu Ser Leu Leu Val Ile Leu Pro Ile Val
                180                 185                 190

Val Phe Ser Arg Thr Ala Ala Asn Ser Asp Gly Thr Val Ala Cys Asn
                195                 200                 205

Met Leu Met Pro Glu Pro Ala Gln Arg Trp Leu Val Gly Phe Val Leu
    210                 215                 220

Tyr Thr Phe Leu Met Gly Phe Leu Leu Pro Val Gly Ala Ile Cys Leu
225                 230                 235                 240

Cys Tyr Val Leu Ile Ile Ala Lys Met Arg Met Val Pro Ser Arg Pro
                245                 250                 255

Ala Gly Ser Thr Gln Arg Ser Glu Arg Lys Ile Thr Leu Met Val Met
                260                 265                 270

Met Val Val Met Val Phe Val Ile Cys Trp Met Pro Phe Tyr Val Val
    275                 280                 285

Gln Leu Val Asn Val Phe Ala Glu Gln Asp Asp Ala Thr Val Ser Gln
290                 295                 300

Leu Ser Val Ile Leu Gly Tyr Ala Asn Ser Cys Ala Asn Pro Ile Leu
305                 310                 315                 320

Tyr Gly Phe Leu Ser Asp Asn Phe Lys Arg Ser Phe Gln Arg Ile Leu
                325                 330                 335

Cys Leu Ser Trp Met Asp Asn Ala Ala Glu Glu Pro Val Asp Tyr Tyr
                340                 345                 350

Ala Thr Ala Leu Lys Ser Arg Ala Tyr Ser Val Glu Asp Phe Gln Pro
                355                 360                 365

Glu Asn Leu Glu Ser Gly Gly Val Phe Arg Asn Gly Thr Cys Ala Ser
    370                 375                 380

Arg Ile Ser Thr Leu
385
```

(2) INFORMATION FOR SEQ ID NO:8:

(i) SEQUENCE CHARACTERISTICS:
        (A) LENGTH: 350 amino acids (B) TYPE: amino acid
(D) TOPOLOGY: linear (ii) MOLECULE TYPE: protein (v) FRAGMENT TYPE: N-terminal (vi) ORIGINAL SOURCE:
    (A) ORGANISM: Homo sapiens (vii) IMMEDIATE SOURCE:
    (B) CLONE: F-PEP (xi) SEQUENCE DESCRIPTION: SEQ ID NO:8:

```
Met Glu Thr Asn Ser Ser Leu Pro Thr Asn Ile Ser Gly Gly Thr Pro
1               5                   10                  15

Ala Val Ser Ala Gly Tyr Leu Phe Leu Asp Ile Ile Thr Tyr Leu Val
            20                  25                  30

Phe Ala Val Thr Phe Val Leu Gly Val Leu Gly Asn Gly Leu Val Ile
            35                  40                  45

Trp Val Ala Gly Phe Arg Met Thr His Thr Val Thr Thr Ile Ser Tyr
    50                  55                  60

Leu Asn Leu Ala Val Ala Asp Phe Cys Phe Thr Ser Thr Leu Pro Phe
65                  70                  75                  80

Phe Met Val Arg Lys Ala Met Gly Gly His Trp Pro Phe Gly Trp Phe
                85                  90                  95

Leu Cys Lys Phe Val Phe Thr Ile Val Asp Ile Asn Leu Phe Gly Ser
                100                 105                 110

Val Phe Leu Ile Ala Leu Ile Ala Leu Asp Arg Cys Val Cys Val Leu
            115                 120                 125

His Pro Val Trp Thr Gln Asn His Arg Thr Val Ser Leu Ala Lys Lys
        130                 135                 140

Val Ile Gly Pro Trp Val Met Ala Leu Leu Leu Thr Leu Pro Val
145                 150                 155                 160

Ile Ile Arg Val Thr Thr Val Pro Gly Lys Thr Gly Thr Val Ala Cys
                165                 170                 175

Thr Phe Asn Phe Ser Pro Trp Thr Asn Asp Pro Lys Glu Arg Ile Lys
            180                 185                 190

Val Ala Val Ala Met Leu Thr Val Arg Gly Ile Ile Arg Gly Ile Ile
        195                 200                 205

Gly Phe Ser Ala Pro Met Ser Ile Val Ala Val Ser Tyr Gly Leu Ile
    210                 215                 220

Ala Thr Lys Ile His Lys Gln Gly Leu Ile Lys Ser Ser Arg Pro Leu
225                 230                 235                 240

Arg Val Leu Ser Phe Val Ala Ala Phe Leu Cys Trp Ser Pro
                245                 250                 255

Tyr Gln Val Val Ala Leu Ile Ala Thr Val Arg Ile Arg Glu Leu Leu
            260                 265                 270

Gln Gly Met Tyr Lys Glu Ile Gly Ile Ala Val Asp Val Thr Ser Ala
        275                 280                 285

Leu Ala Phe Phe Asn Ser Cys Leu Asn Pro Met Leu Tyr Val Phe Met
    290                 295                 300

Gly Gln Asp Phe Arg Glu Arg Leu Ile His Ala Leu Pro Ala Ser Leu
305                 310                 315                 320

Glu Arg Ala Leu Thr Glu Asp Ser Thr Gln Thr Ser Asp Thr Ala Thr
                325                 330                 335

Asn Ser Thr Leu Pro Ser Ala Glu Val Ala Leu Gln Ala Lys
```

(2) INFORMATION FOR SEQ ID NO:9:

(i) SEQUENCE CHARACTERISTICS:
        (A) LENGTH: 440 amino acids
        (B) TYPE: amino acid
        (C) STRANDEDNESS: single
        (D) TOPOLOGY: linear (v) FRAGMENT TYPE: N-terminal (vi) ORIGINAL SOURCE:
        (A) ORGANISM: Homo sapiens (vii) IMMEDIATE SOURCE:
        (B) CLONE: OPB-R (xi) SEQUENCE DESCRIPTION: SEQ ID NO:9:

```
Met Ala Ser Pro Ala Gly Asn Leu Ser Ala Trp Pro Gly Trp Gly Trp
 1               5                  10                  15

Pro Pro Pro Ala Ala Leu Arg Asn Leu Thr Ser Ser Pro Ala Pro Thr
                20                  25                  30

Ala Ser Pro Ser Pro Ala Pro Ser Trp Thr Pro Ser Pro Arg Pro Gly
            35                  40                  45

Pro Ala His Pro Phe Leu Gln Pro Pro Trp Ala Val Ala Leu Trp Ser
50                  55                  60

Leu Ala Tyr Gly Ala Val Val Ala Val Ala Val Leu Gly Asn Leu Val
65                  70                  75                  80

Val Ile Trp Ile Val Leu Ala His Lys Arg Met Arg Thr Val Thr Asn
                85                  90                  95

Ser Phe Leu Val Asn Leu Ala Phe Ala Asp Ala Ala Met Ala Ala Leu
                100                 105                 110

Asn Ala Leu Val Asn Phe Ile Tyr Ala Leu His Gly Glu Trp Tyr Phe
            115                 120                 125

Gly Ala Asn Tyr Cys Arg Phe Gln Asn Phe Phe Pro Ile Thr Ala Val
        130                 135                 140

Phe Ala Ser Ile Tyr Ser Met Thr Ala Ile Ala Val Asp Arg Tyr Met
145                 150                 155                 160

Ala Ile Ile Asp Pro Leu Lys Pro Arg Leu Ser Ala Thr Ala Thr Arg
                165                 170                 175

Ile Val Ile Gly Ser Ile Trp Ile Leu Ala Phe Leu Leu Ala Phe Pro
            180                 185                 190

Gln Cys Leu Tyr Ser Lys Ile Lys Val Met Pro Gly Arg Thr Leu Cys
        195                 200                 205

Tyr Val Gln Trp Pro Glu Gly Ser Arg Gln His Phe Thr Tyr His Met
210                 215                 220

Ile Val Ile Val Leu Val Tyr Cys Phe Pro Leu Leu Ile Met Gly Ile
225                 230                 235                 240

Thr Tyr Thr Ile Val Gly Ile Thr Leu Trp Gly Gly Glu Ile Pro Gly
                245                 250                 255

Asp Thr Cys Asp Lys Tyr Gln Glu Gln Leu Lys Ala Lys Arg Lys Val
            260                 265                 270

Val Lys Met Met Ile Ile Val Val Thr Phe Ala Ile Cys Trp Leu
        275                 280                 285

Pro Tyr His Ile Tyr Phe Ile Leu Thr Ala Ile Tyr Gln Gln Leu Asn
290                 295                 300

Arg Trp Lys Tyr Ile Gln Gln Val Tyr Leu Ala Ser Phe Trp Leu Ala
```

```
305                 310                 315                 320
Met Ser Ser Thr Met Tyr Asn Pro Ile Ile Tyr Cys Cys Leu Asn Lys
                325                 330                 335

Arg Phe Arg Ala Gly Phe Lys Arg Ala Phe Arg Trp Cys Pro Phe Ile
            340                 345                 350

His Val Ser Ser Tyr Asp Glu Leu Glu Leu Lys Ala Thr Arg Leu His
            355                 360                 365

Pro Met Arg Gln Ser Ser Leu Tyr Thr Val Thr Arg Met Glu Ser Met
        370                 375                 380

Ser Val Val Phe Asp Ser Asn Asp Gly Asp Ser Ala Arg Ser Ser His
385                 390                 395                 400

Gln Lys Arg Gly Thr Thr Arg Asp Val Gly Ser Asn Val Cys Ser Arg
            405                 410                 415

Arg Asn Ser Lys Ser Thr Ser Thr Thr Ala Ser Phe Val Ser Ser Ser
            420                 425                 430

His Met Ser Val Glu Glu Gly Ser
        435                 440
```

(2) INFORMATION FOR SEQ ID NO:10:

(i) SEQUENCE CHARACTERISTICS:
        (A) LENGTH: 451 amino acids
        (B) TYPE: amino acid
        (C) STRANDEDNESS: single
        (D) TOPOLOGY: linear (ii) MOLECULE TYPE: protein (v) FRAGMENT TYPE: N-terminal (vi) ORIGINAL SOURCE:
        (A) ORGANISM: Rattus rattus (vii) IMMEDIATE SOURCE:
        (B) CLONE: NEU-K (xi) SEQUENCE DESCRIPTION: SEQ ID NO:10:

```
Met Ala Ser Val Pro Arg Gly Glu Asn Trp Thr Asp Gly Thr Val Glu
1               5                   10                  15

Val Gly Thr His Thr Gly Asn Leu Ser Ser Ala Leu Gly Val Thr Glu
            20                  25                  30

Trp Leu Ala Leu Gln Ala Gly Asn Phe Ser Ser Ala Leu Gly Leu Pro
        35                  40                  45

Ala Thr Thr Gln Ala Pro Ser Gln Val Arg Ala Asn Leu Thr Asn Gln
    50                  55                  60

Phe Val Gln Pro Ser Trp Arg Ile Ala Leu Trp Ser Leu Ala Tyr Gly
65                  70                  75                  80

Leu Val Val Ala Val Ala Val Phe Gly Asn Leu Ile Val Ile Trp Ile
                85                  90                  95

Ile Leu Ala His Lys Arg Met Arg Thr Val Thr Asn Tyr Phe Leu Val
            100                 105                 110

Asn Leu Ala Phe Ser Asp Ala Ser Val Ala Ala Phe Asn Thr Leu Ile
            115                 120                 125

Asn Phe Ile Tyr Gly Leu His Ser Glu Trp Tyr Phe Gly Ala Asn Tyr
        130                 135                 140

Cys Arg Phe Gln Asn Phe Phe Pro Ile Thr Ala Val Phe Ala Ser Ile
145                 150                 155                 160

Tyr Ser Met Thr Ala Ile Ala Val Asp Arg Tyr Met Ala Ile Ile Asp
                165                 170                 175
```

```
Pro Leu Lys Pro Arg Leu Ser Ala Thr Ala Thr Lys Ile Val Ile Gly
            180                 185                 190

Ser Ile Trp Ile Leu Ala Phe Leu Leu Ala Phe Pro Gln Cys Leu Tyr
        195                 200                 205

Ser Lys Ile Lys Val Met Pro Gly Arg Thr Leu Cys Tyr Val Gln Trp
        210                 215                 220

Pro Glu Gly Pro Lys Gln His Phe Thr Tyr His Ile Ile Val Ile Ile
225                 230                 235                 240

Leu Val Tyr Cys Phe Pro Leu Leu Ile Met Gly Val Thr Tyr Thr Ile
                245                 250                 255

Val Gly Ile Thr Leu Trp Gly Gly Glu Ile Pro Gly Asp Thr Cys Asp
            260                 265                 270

Lys Tyr His Glu Gln Leu Lys Ala Lys Arg Lys Val Val Lys Met Met
            275                 280                 285

Ile Ile Val Val Thr Phe Ala Ile Cys Trp Leu Pro Tyr His Val Tyr
            290                 295                 300

Phe Ile Leu Thr Ala Ile Tyr Gln Gln Leu Asn Arg Trp Lys Tyr Ile
305                 310                 315                 320

Gln Gln Val Tyr Leu Ala Ser Phe Trp Leu Ala Met Ser Ser Thr Met
                325                 330                 335

Tyr Asn Pro Ile Ile Tyr Cys Cys Leu Asn Lys Arg Phe Arg Ala Gly
            340                 345                 350

Phe Lys Arg Ala Phe Arg Trp Cys Pro Phe Ile Gln Val Ser Ser Tyr
            355                 360                 365

Asp Glu Leu Glu Leu Lys Thr Thr Arg Phe His Pro Thr Arg Gln Ser
            370                 375                 380

Ser Leu Tyr Thr Val Ser Arg Met Glu Ser Val Thr Val Leu Phe Asp
385                 390                 395                 400

Pro Asn Asp Gly Asp Pro Thr Lys Ser Ser Arg Lys Lys Arg Ala Val
                405                 410                 415

Pro Arg Asp Pro Ser Ala Asn Gly Cys Ser His Arg Gly Ser Lys Ser
            420                 425                 430

Ala Ser Thr Thr Ser Ser Phe Ile Ser Ser Pro Tyr Thr Ser Val Asp
            435                 440                 445

Glu Tyr Ser
    450

(2) INFORMATION FOR SEQ ID NO:11:

(i) SEQUENCE CHARACTERISTICS:
         (A) LENGTH: 348 amino acids
         (B) TYPE: amino acid
         (D) TOPOLOGY: linear (ii) MOLECULE TYPE: protein (v) FRAGMENT TYPE: N-terminal (vi) ORIGINAL SOURCE:
         (A) ORGANISM: Rattus rattus (vii) IMMEDIATE SOURCE:
         (B) CLONE: RHODOP (xi) SEQUENCE DESCRIPTION: SEQ ID NO:11:

Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
```

```
                    20                  25                  30
Glu Pro Trp Gln Phe Ser Met Leu Ala Ala Tyr Met Phe Leu Leu Ile
            35                  40                  45

Val Leu Gly Phe Pro Ile Asn Phe Leu Thr Leu Tyr Val Thr Val Gln
 50                  55                  60

His Lys Lys Leu Arg Thr Pro Leu Asn Tyr Ile Leu Leu Asn Leu Ala
 65                  70                  75                  80

Val Ala Asp Leu Phe Met Val Phe Gly Gly Phe Thr Thr Thr Leu Tyr
                 85                  90                  95

Thr Ser Leu His Gly Tyr Phe Val Phe Gly Pro Thr Gly Cys Asn Leu
                100                 105                 110

Glu Gly Phe Phe Ala Thr Leu Gly Gly Glu Ile Ala Leu Trp Ser Leu
                115                 120                 125

Val Val Leu Ala Ile Glu Arg Tyr Val Val Ile Cys Lys Pro Met Ser
130                 135                 140

Asn Phe Arg Phe Gly Glu Asn His Ala Ile Met Gly Val Val Phe Thr
145                 150                 155                 160

Trp Ile Met Ala Leu Ala Cys Ala Ala Pro Pro Leu Val Gly Trp Ser
                165                 170                 175

Arg Tyr Ile Pro Glu Gly Met Gln Cys Ser Cys Gly Val Asp Tyr Tyr
                180                 185                 190

Thr Leu Lys Pro Glu Val Asn Asn Glu Ser Phe Val Ile Tyr Met Phe
                195                 200                 205

Val Val His Phe Thr Ile Pro Leu Ile Val Ile Phe Phe Cys Tyr Gly
                210                 215                 220

Gln Leu Val Phe Thr Val Lys Glu Ala Ala Ala Gln Gln Gln Glu Ser
225                 230                 235                 240

Ala Thr Thr Gln Lys Ala Glu Lys Glu Val Thr Arg Met Val Ile Leu
                245                 250                 255

Met Val Val Phe Phe Leu Ile Cys Trp Phe Pro Tyr Ala Gly Val Ala
                260                 265                 270

Phe Tyr Ile Phe Thr His Gln Gly Ser Asn Phe Gly Phe Ile Phe Met
                275                 280                 285

Thr Leu Pro Ala Phe Phe Ala Lys Ser Ser Ser Ile Tyr Asn Pro Val
                290                 295                 300

Ile Tyr Ile Met Met Asn Lys Gln Phe Arg Asn Cys Met Leu Thr Thr
305                 310                 315                 320

Leu Cys Cys Gly Lys Asn Ile Leu Gly Asp Asp Glu Ala Ser Ala Thr
                325                 330                 335

Ala Ser Lys Thr Glu Thr Ser Gln Val Ala Pro Ala
                340                 345
```

(2) INFORMATION FOR SEQ ID NO:12:

(i) SEQUENCE CHARACTERISTICS:
        (A) LENGTH: 417 amino acids
        (B) TYPE: amino acid
        (D) TOPOLOGY: linear (ii) MOLECULE TYPE: protein (v) FRAGMENT TYPE: N-terminal (vi) ORIGINAL SOURCE:
        (A) ORGANISM: Rattus rattus (vii) IMMEDIATE SOURCE:
        (B) CLONE: B2-ADR (xi) SEQUENCE DESCRIPTION: SEQ ID NO:12:

Met Glu Pro His Gly Asn Asp Ser Asp Phe Leu Leu Ala Pro Asn Gly
1               5                   10                  15

Ser Arg Ala Pro Gly His Asp Ile Thr Gln Glu Arg Asp Glu Ala Trp
                20                  25                  30

Val Val Gly Met Ala Ile Leu Met Ser Val Ile Val Leu Ala Ile Val
            35                  40                  45

Phe Gly Asn Val Leu Val Ile Thr Ala Ile Ala Lys Phe Glu Arg Leu
        50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ser His Ile Leu Met
                85                  90                  95

Lys Met Trp Asn Phe Gly Asn Phe Trp Cys Glu Phe Trp Thr Ser Ile
                100                 105                 110

Asp Val Leu Cys Val Thr Ala Ser Ile Glu Thr Leu Cys Val Ile Ala
            115                 120                 125

Val Asp Arg Tyr Val Ala Ile Thr Ser Pro Phe Lys Tyr Gln Ser Leu
        130                 135                 140

Leu Thr Lys Asn Lys Ala Arg Val Val Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Lys Gln Ala Ile Asp Cys Tyr Ala Lys Glu Thr Cys Cys Asp
                180                 185                 190

Phe Phe Thr Asn Gln Ala Tyr Ala Ile Ala Ser Ser Ile Val Ser Phe
            195                 200                 205

Tyr Val Pro Leu Val Val Met Val Phe Val Tyr Ser Arg Val Phe Gln
        210                 215                 220

Val Ala Lys Arg Gln Leu Gln Lys Ile Asp Lys Ser Glu Gly Arg Phe
225                 230                 235                 240

His Ala Gln Asn Leu Ser Gln Val Glu Gln Asp Gly Arg Ser Gly His
                245                 250                 255

Gly Leu Arg Ser Ser Lys Phe Cys Leu Lys Glu His Lys Ala Leu
                260                 265                 270

Lys Thr Leu Gly Ile Ile Met Gly Thr Phe Thr Leu Cys Trp Leu Pro
                275                 280                 285

Phe Phe Ile Val Asn Ile Val His Val Ile Arg Ala Asn Leu Ile Pro
        290                 295                 300

Lys Glu Val Tyr Ile Leu Leu Asn Trp Leu Gly Tyr Val Asn Ser Ala
305                 310                 315                 320

Phe Asn Pro Leu Ile Tyr Cys Arg Ser Pro Asp Arg Ile Ala Phe Gln
                325                 330                 335

Glu Leu Leu Cys Leu Arg Arg Ser Ser Lys Thr Tyr Gly Asn Gly
            340                 345                 350

Tyr Ser Ser Asn Ser Asn Gly Arg Thr Asp Tyr Thr Gly Glu Gln Ser
        355                 360                 365

Ala Tyr Gln Leu Gly Gln Glu Lys Glu Asn Glu Leu Leu Cys Glu Glu
        370                 375                 380

Ala Pro Gly Met Glu Gly Phe Val Asn Cys Gln Gly Thr Val Pro Ser
385                 390                 395                 400

Leu Ser Ile Asp Ser Gln Gly Arg Asn Cys Asn Thr Asn Asp Ser Pro

-continued

```
                    405                 410                 415
Leu (2) INFORMATION FOR SEQ ID NO:13:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(ix) FEATURE:
        (A) NAME/KEY: Other
        (B) LOCATION: 32...32
        (D) OTHER INFORMATION: Lysine at position 32 is biotinylated (xi) SEQUENCE DESCRIPTION: SEQ ID NO:13:

Tyr Gly Gly Phe Met Thr Ser Glu Lys Ser Gln Thr Pro Leu Val Thr
 1               5                  10                  15

Leu Phe Lys Asn Ala Ile Ile Lys Asn Ala Tyr Lys Lys Gly Glu Lys
            20                  25                  30

(2) INFORMATION FOR SEQ ID NO:14:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:14:

Lys Glu Lys Asp Arg Asn Leu Arg Arg Ile Thr Arg Met Val Leu Val
 1               5                  10                  15

Val Val Ala Val Phe Ile Val
            20
```

What is claimed is:

1. An isolated purified nucleic acid sequence encoding a mu-subtype opioid receptor consisting of the sequence depicted in FIG. 11, SEQ ID NO:1.

2. An isolated purified nucleic acid sequence which encodes a receptor having the amino acid sequence of FIG. 9 SEQ ID NO:2.

3. A mammalian expression vector comprising an isolated nucleic acid sequence as defined in claim 2.

4. A cell transformed with an isolated, purified nucleic acid sequence as defined in claim 2.

5. A mammalian cell comprising a vector as defined in claim 3.

6. A method for producing a mu-subtype opioid receptor, said method comprising:
   (a) culturing a mammalian cell as defined in claim 5 in a culturing medium suitable for expression of said receptor;
   (b) expressing said receptor; and
   (c) isolating said receptor from the cultured cells.

* * * * *

UNITED STATES PATENT AND TRADEMARK OFFICE
CERTIFICATE OF CORRECTION

PATENT NO. : 6,225,080 B1
DATED : May 1, 2001
INVENTOR(S) : George R. Uhl, Mark Eppler and Jai-Bei Wang It is certified that error appears in the above-identified patent and that said Letters Patent is hereby corrected as shown below:

<u>Title page,</u>
Item [75], Inventors, change "Jai-Bel Wang" to -- Jai-Bei Wang --

Signed and Sealed this

Thirty-first Day of May, 2005

JON W. DUDAS
*Director of the United States Patent and Trademark Office*